US007470920B2

(12) United States Patent
Gorrell et al.

(10) Patent No.: US 7,470,920 B2
(45) Date of Patent: Dec. 30, 2008

(54) RESONANT STRUCTURE-BASED DISPLAY

(75) Inventors: Jonathan Gorrell, Gainesville, FL (US); Mark Davidson, Florahome, FL (US); Michael E Maines, Gainesville, FL (US)

(73) Assignee: Virgin Islands Microsystems, Inc. VI (US)

( * ) Notice: Subject to any disclaimer, the term of this patent is extended or adjusted under 35 U.S.C. 154(b) by 542 days.

(21) Appl. No.: 11/325,432

(22) Filed: Jan. 5, 2006

(65) Prior Publication Data

US 2007/0152938 A1 Jul. 5, 2007

(51) Int. Cl.
*A61N 5/06* (2006.01)

(52) U.S. Cl. .............................. 250/494.1; 250/492.23; 250/396 R; 977/950; 455/323; 455/329

(58) Field of Classification Search ............. 250/494.1, 250/492.23, 396 R, 493.1, 400; 977/950; 455/323, 329, 313, 325; 359/295; 310/305, 310/308; 348/E5.143–E5.145
See application file for complete search history.

(56) References Cited

U.S. PATENT DOCUMENTS

| | | | |
|---|---|---|---|
| 1,948,384 | A | 2/1934 | Lawrence |
| 2,307,086 | A | 1/1943 | Varian et al. |
| 2,431,396 | A | 11/1947 | Hansell |
| 2,473,477 | A | 6/1949 | Smith |
| 2,634,372 | A | 4/1953 | Salisbury |
| 2,932,798 | A | 4/1960 | Kerst et al. |
| 2,944,183 | A | 7/1960 | Drexler |
| 2,966,611 | A | 12/1960 | Sandstrom |
| 3,231,779 | A | 1/1966 | White |
| 3,297,905 | A | 1/1967 | Fiedor et al. |
| 3,543,147 | A | 11/1970 | Kovarik |
| 3,571,642 | A | 3/1971 | Westcott |
| 3,586,899 | A | 6/1971 | Fleisher |
| 3,761,828 | A | 9/1973 | Pollard et al. |
| 3,886,399 | A | 5/1975 | Symons |
| 3,923,568 | A | 12/1975 | Bersin |
| 3,989,347 | A | 11/1976 | Eschler |

(Continued)

FOREIGN PATENT DOCUMENTS

| | | | |
|---|---|---|---|
| EP | 0237559 | B1 | 12/1991 |

(Continued)

OTHER PUBLICATIONS

Mokhoff, Nicolas, "Optical-speed light detector promises fast space talk," EETimes Online, Mar. 20, 2006, from website: www.eetimes.com/showArticle.jhtml?articleID=183701047.

(Continued)

*Primary Examiner*—Haissa Philogene
(74) *Attorney, Agent, or Firm*—Davidson Berquist Jackson & Gowdey LLP

(57) ABSTRACT

A display of wavelength elements can be produced from resonant structures that emit light (and other electromagnetic radiation having a dominant frequency higher than that of microwave) when exposed to a beam of charged particles, such as electrons from an electron beam. An exemplary display with three wavelengths per pixel utilizes three resonant structures per pixel. The spacings and lengths of the fingers of the resonant structures control the light emitted from the wavelength elements. Alternatively, multiple resonant structures per wavelength can be used as well.

16 Claims, 28 Drawing Sheets

U.S. PATENT DOCUMENTS 4,282,436 A 8/1981 Kapetanakos et al.
4,482,779 A 11/1984 Anderson
4,712,042 A 12/1987 Hamm
4,713,581 A 12/1987 Haimson
4,727,550 A 2/1988 Chang et al.
4,740,973 A 4/1988 Madey
4,746,201 A 5/1988 Gould
4,829,527 A 5/1989 Wortman et al.
4,838,021 A 6/1989 Beattie
4,864,131 A 9/1989 Rich et al.
5,023,563 A 6/1991 Harvey et al.
5,113,141 A 5/1992 Swenson
5,128,729 A 7/1992 Alonas et al.
5,157,000 A 10/1992 Elkind et al.
5,163,118 A 11/1992 Lorenzo et al.
5,185,073 A 2/1993 Bindra et al.
5,199,918 A 4/1993 Kumar
5,235,248 A 8/1993 Clark et al.
5,262,656 A 11/1993 Blondeau et al.
5,263,043 A 11/1993 Walsh
5,268,693 A 12/1993 Walsh
5,268,788 A 12/1993 Fox et al.
5,302,240 A 4/1994 Hori et al.
5,354,709 A 10/1994 Lorenzo et al.
5,446,814 A 8/1995 Kuo et al.
5,504,341 A 4/1996 Glavish
5,578,909 A 11/1996 Billen
5,608,263 A 3/1997 Drayton et al.
5,666,020 A 9/1997 Takemura
5,668,368 A 9/1997 Sakai et al.
5,705,443 A 1/1998 Stauf et al.
5,737,458 A 4/1998 Wojnarowski et al.
5,744,919 A 4/1998 Mishin et al.
5,757,009 A 5/1998 Walstrom
5,767,013 A 6/1998 Park
5,790,585 A 8/1998 Walsh
5,811,943 A 9/1998 Mishin et al.
5,821,836 A 10/1998 Katehi et al.
5,821,902 A 10/1998 Keen
5,825,140 A 10/1998 Fujisawa
5,831,270 A 11/1998 Nakasuji
5,847,745 A 12/1998 Shimizu et al.
5,889,449 A 3/1999 Fiedziuszko
5,902,489 A 5/1999 Yasuda et al.
6,008,496 A 12/1999 Winefordner et al.
6,040,625 A 3/2000 Ip
6,060,833 A 5/2000 Velazco
6,080,529 A 6/2000 Ye et al.
6,139,760 A 10/2000 Shim et al.
6,180,415 B1 * 1/2001 Schultz et al. .............. 436/518
6,195,199 B1 2/2001 Yamada
6,222,866 B1 4/2001 Seko
6,278,239 B1 8/2001 Caporaso et al.
6,281,769 B1 8/2001 Fiedziuszko
6,297,511 B1 10/2001 Syllaios et al.
6,316,876 B1 11/2001 Tanabe
6,338,968 B1 1/2002 Hefti
6,370,306 B1 4/2002 Sato et al.
6,373,194 B1 4/2002 Small
6,376,258 B2 4/2002 Hefti
6,407,516 B1 6/2002 Victor
6,441,298 B1 8/2002 Thio
6,453,087 B2 9/2002 Frish et al.
6,470,198 B1 10/2002 Kintaka et al.
6,504,303 B2 1/2003 Small
6,525,477 B2 2/2003 Small
6,545,425 B2 4/2003 Victor
6,577,040 B2 6/2003 Nguyen
6,603,915 B2 8/2003 Glebov et al.
6,624,916 B1 9/2003 Green et al.
6,636,185 B1 * 10/2003 Spitzer et al. .................. 345/8
6,636,653 B2 10/2003 Miracky et al.
6,640,023 B2 10/2003 Miller et al.
6,642,907 B2 11/2003 Hamada et al.
6,687,034 B2 * 2/2004 Wine et al. .................. 359/198
6,738,176 B2 5/2004 Rabinowitz et al.
6,741,781 B2 5/2004 Furuyama
6,782,205 B2 8/2004 Trisnadi et al.
6,791,438 B2 9/2004 Takahashi et al.
6,829,286 B1 12/2004 Guilfoyle et al.
6,834,152 B2 12/2004 Gunn et al.
6,870,438 B1 3/2005 Shino et al.
6,885,262 B2 4/2005 Nishimura et al.
6,909,092 B2 6/2005 Nagahama et al.
6,909,104 B1 6/2005 Koops
6,943,650 B2 9/2005 Ramprasad et al.
6,944,369 B2 9/2005 Deliwala
6,953,291 B2 10/2005 Liu
6,954,515 B2 10/2005 Bjorkholm et al.
6,965,284 B2 11/2005 Maekawa et al.
6,965,625 B2 11/2005 Mross et al.
6,972,439 B1 12/2005 Kim et al.
6,995,406 B2 2/2006 Tojo et al.
7,010,183 B2 3/2006 Estes et al.
7,092,588 B2 8/2006 Kondo
7,092,603 B2 8/2006 Glebov et al.
7,122,978 B2 10/2006 Nakanishi et al.
7,177,515 B2 2/2007 Estes et al.
7,230,201 B1 6/2007 Miley
7,267,459 B2 9/2007 Matheson
7,267,461 B2 9/2007 Kan et al.
7,342,441 B2 3/2008 Gorrell et al.
2001/0025925 A1 10/2001 Abe et al.
2002/0009723 A1 1/2002 Hefti
2002/0027481 A1 3/2002 Fiedziuszko
2002/0036121 A1 3/2002 Ball et al.
2002/0036264 A1 3/2002 Nakasuji et al.
2002/0053638 A1 5/2002 Winkler et al.
2002/0070671 A1 6/2002 Small
2002/0071457 A1 6/2002 Hogan
2002/0135665 A1 9/2002 Gardner
2003/0012925 A1 1/2003 Gorrell
2003/0016412 A1 1/2003 Small
2003/0016421 A1 1/2003 Small
2003/0034535 A1 2/2003 Barenburu et al.
2003/0155521 A1 8/2003 Feuerbaum
2003/0158474 A1 8/2003 Scherer et al.
2003/0164947 A1 9/2003 Vaupel
2003/0179974 A1 9/2003 Estes et al.
2003/0206708 A1 11/2003 Estes et al.
2003/0214695 A1 11/2003 Abramson et al.
2004/0061053 A1 4/2004 Taniguchi et al.
2004/0085159 A1 5/2004 Kubena et al.
2004/0108473 A1 6/2004 Melnychuk et al.
2004/0136715 A1 7/2004 Kondo
2004/0150991 A1 8/2004 Ouderkirk et al.
2004/0171272 A1 9/2004 Jin et al.
2004/0180244 A1 9/2004 Tour et al.
2004/0184270 A1 9/2004 Halter
2004/0213375 A1 10/2004 Bjorkholm et al.
2004/0217297 A1 11/2004 Moses et al.
2004/0231996 A1 11/2004 Webb
2004/0240035 A1 12/2004 Zhilkov
2004/0264867 A1 12/2004 Kondo
2005/0023145 A1 2/2005 Cohen et al.
2005/0045821 A1 3/2005 Noji et al.
2005/0045832 A1 3/2005 Kelly et al.
2005/0054151 A1 3/2005 Lowther et al.
2005/0067286 A1 3/2005 Ahn et al.
2005/0082469 A1 4/2005 Carlo
2005/0092929 A1 5/2005 Schneiker
2005/0105690 A1 5/2005 Pau et al.
2005/0145882 A1 7/2005 Taylor et al.
2005/0162104 A1 7/2005 Victor et al.

| | | | |
|---|---|---|---|
| 2005/0190637 | A1 | 9/2005 | Ichimura et al. |
| 2005/0194258 | A1 | 9/2005 | Cohen et al. |
| 2005/0201707 | A1 | 9/2005 | Glebov et al. |
| 2005/0201717 | A1 | 9/2005 | Matsumura et al. |
| 2005/0212503 | A1 | 9/2005 | Deibele |
| 2005/0231138 | A1 | 10/2005 | Nakanishi et al. |
| 2005/0249451 | A1 | 11/2005 | Baehr-Jones et al. |
| 2005/0285541 | A1 | 12/2005 | LeChevalier |
| 2006/0007730 | A1 | 1/2006 | Nakamura et al. |
| 2006/0018619 | A1 | 1/2006 | Helffrich et al. |
| 2006/0035173 | A1 | 2/2006 | Davidson et al. |
| 2006/0045418 | A1 | 3/2006 | Cho et al. |
| 2006/0060782 | A1 | 3/2006 | Khursheed |
| 2006/0062258 | A1 | 3/2006 | Brau et al. |
| 2006/0159131 | A1 | 7/2006 | Liu et al. |
| 2006/0164496 | A1 | 7/2006 | Tokutake et al. |
| 2006/0208667 | A1 | 9/2006 | Lys et al. |
| 2006/0216940 | A1 | 9/2006 | Gorrell et al. |
| 2006/0243925 | A1 | 11/2006 | Barker et al. |
| 2006/0274922 | A1 | 12/2006 | Ragsdale |
| 2007/0003781 | A1 | 1/2007 | de Rochemont |
| 2007/0013765 | A1 | 1/2007 | Hudson et al. |
| 2007/0075264 | A1 | 4/2007 | Gorrell et al. |
| 2007/0086915 | A1 | 4/2007 | LeBoeuf et al. |
| 2007/0116420 | A1 | 5/2007 | Estes et al. |
| 2007/0284527 | A1 | 12/2007 | Zani et al. |

FOREIGN PATENT DOCUMENTS

| | | | |
|---|---|---|---|
| JP | 2004-32323 | A | 1/2004 |
| WO | WO 87/01873 | | 3/1987 |
| WO | WO 93/21663 | A1 | 10/1993 |
| WO | WO 00/72413 | | 11/2000 |
| WO | WO 02/25785 | | 3/2002 |
| WO | WO 02/077607 | | 10/2002 |
| WO | WO 2004/086560 | | 10/2004 |
| WO | WO 2005/015143 | A2 | 2/2005 |
| WO | WO 2006/042239 | A2 | 4/2006 |
| WO | WO 2007/081389 | | 7/2007 |
| WO | WO 2007/081390 | | 7/2007 |
| WO | WO 2007/081391 | | 7/2007 |

OTHER PUBLICATIONS

Lee Kwang-Cheol et al., "Deep X-Ray Mask with Integrated Actuator for 3D Microfabrication", Conference: Pacific Rim Workshop on Transducers and Micro/Nano Technologies, (Xiamen CHN), Jul. 22, 2002.

Markoff, John, "A Chip That Can Transfer Data Using Laser Light," The New York Times, Sep. 18, 2006.

S.M. Sze, "Semiconductor Devices Physics and Technology", 2nd Edition, Chapters 9 and 12, Copyright 1985, 2002.

Search Report and Written Opinion mailed Feb. 12, 2007 in PCT Appln. No. PCT/US2006/022682.

Search Report and Written Opinion mailed Feb. 20, 2007 in PCT Appln. No. PCT/US2006/022676.

Search Report and Written Opinion mailed Feb. 20, 2007 in PCT Appln. No. PCT/US2006/022772.

Search Report and Written Opinion mailed Feb. 20, 2007 in PCT Appln. No. PCT/US2006/022780.

Search Report and Written Opinion mailed Feb. 21, 2007 in PCT Appln. No. PCT/US2006/022684.

Search Report and Written Opinion mailed Jan. 17, 2007 in PCT Appln. No. PCT/US2006/022777.

Search Report and Written Opinion mailed Jan. 23, 2007 in PCT Appln. No. PCT/US2006/022781.

Search Report and Written Opinion mailed Mar. 7, 2007 in PCT Appln. No. PCT/US2006/022775.

Speller et al., "A Low-Noise MEMS Accelerometer for Unattended Ground Sensor Applications", Applied MEMS Inc.; 12200 Parc Crest, Stafford, TX, USA 77477.

Thurn-Albrecht et al., "Ultrahigh-Density Nanowire Arrays Grown in Self-Assembled Diblock Copolymer Templates", Science 290.5499, Dec. 15, 2000, pp. 2126-2129.

International Search Report and Written Opinio mailed Nov. 23, 2007 in International Application No. PCT/US2006/022786.

Search Report and Written Opinion mailed Oct. 25, 2007 in PCT Appln. No. PCT/US2006/022687.

Search Report and Written Opinion mailed Oct. 26, 2007 in PCT Appln. No. PCT/US2006/022675.

Search Report and Written Opinion mailed Sep. 21, 2007 in PCT Appln. No. PCT/US2006/022688.

Search Report and Written Opinion mailed Sep. 25, 2007 in PCT appln. No. PCT/US2006/022681.

Search Report and Written Opinion mailed Sep. 26, 2007 in PCT Appln. No. PCT/US2006/024218.

Search Report and Written Opinion mailed Apr. 23, 2008 in PCT Appln. No. PCT/US2006/022678.

Search Report and Written Opinion mailed Apr. 3, 2008 in PCT Appln. No. PCT/US2006/027429.

Search Report and Written Opinion mailed Jun. 18, 2008 in PCT Appln. No. PCT/US2006/027430.

Search Report and Written Opinion mailed Jun. 3, 2008 in PCT Appln. No. PCT/US2006/022783.

Search Report and Written Opinion mailed Mar. 24, 2008 in PCT Appln. No. PCT/US2006/022677.

Search Report and Written Opinion mailed Mar. 24, 2008 in PCT Appln. No. PCT/US2006/022784.

Search Report and Written Opinion mailed May 2, 2008 in PCT Appln. No. PCT/US2006/023280.

Search Report and Written Opinion mailed May 21, 2008 in PCT Appln. No. PCT/US2006/023279.

Search Report and Written Opinion mailed May 22, 2008 in PCT Appln. No. PCT/US2006/022685.

U.S. Appl. No. 11/418,082, filed May 5, 2006, Gorrell et al.

J. C. Palais, "Fiber optic communications," Prentice Hall, New Jersey, 1998, pp. 156-158.

Search Report and Written Opinion mailed Dec. 20, 2007 in PCT Appln. No. PCT/US2006/022771.

Search Report and Written Opinion mailed Jan. 31, 2008 in PCT Appln. No. PCT/US2006/027427.

Search Report and Written Opinion mailed Jan. 8, 2008 in PCT Appln. No. PCT/US2006/028741.

Search Report and Written Opinion mailed Mar. 11, 2008 in PCT Appln. No. PCT/US2006/022679.

Search Report and Written Opinion mailed Aug. 24, 2007 in PCT Appln. No. PCT/US2006/022768.

Search Report and Written Opinion mailed Aug. 31, 2007 in PCT Appln. No. PCT/US2006/022680.

Search Report and Written Opinion mailed Jul. 16, 2007 in PCT Appln. No. PCT/US2006/022774.

Search Report and Written Opinion mailed Jul. 20, 2007 in PCT Appln. No. PCT/US2006/024216.

Search Report and Written Opinion mailed Jul. 26, 2007 in PCT Appln. No. PCT/US2006/022776.

Search Report and Written Opinion mailed Jun. 20, 2007 in PCT Appln. No. PCT/US2006/022779.

Search Report and Written Opinion mailed Sep. 12, 2007 in PCT Appln. No. PCT/US2006/022767.

Search Report and Written Opinion mailed Sep. 13, 2007 in PCT Appln. No. PCT/US2006/024217.

Search Report and Written Opinion mailed Sep. 17, 2007 in PCT Appln. No. PCT/US2006/022787.

Search Report and Written Opinion mailed Sep. 5, 2007 in PCT Appln. No. PCT/US2006/027428.

Search Report and Written Opinion mailed Sep. 17, 2007 in PCT Appln. No. PCT/US2006/022689.

S. Hoogland et al., "A solution-processed 1.53 μm quantum dot laser with temperature-invariant emission wavelength," Optics Express, vol. 14, No. 8, Apr. 17, 2006, pp. 3273-3281.

"Array of Nanoklystrons for Frequency Agility or Redundancy," NASA's Jet Propulsion Laboratory, NASA Tech Briefs, NPO-21033. 2001.

"Hardware Development Programs," Calabazas Creek Research, Inc. found ar http://calcreek.com/hardware.html.

"Antenna Arrays." May 18, 2002. www.tpub.com/content/neets/14183/css/14183_159.htm.

"Diffraction Grating," hyperphysics.phy-astr.gsu.edu/hbase/phyopt/grating.html.
Alford, T.L. et al., "Advanced silver-based metallization patterning for ULSI applications," Microelectronic Engineering 55, 2001, pp. 383-388, Elsevier Science B.V.
Amato, Ivan, "An Everyman's Free-Electron Laser?" Science, New Series, Oct. 16, 1992, p. 401, vol. 258 No. 5081, American Association for the Advancement of Science.
Andrews, H.L. et al., "Dispersion and Attenuation in a Smith-Purcell Free Electron Laser," The American Physical Society, Physical Review Special Topics—Accelerators and Beams 8 (2005), pp. 050703-1—050703-9.
Backe, H. et al. "Investigation of Far-Infrared Smith-Purcell Radiation at the 3.41 MeV Electron Injector Linac of the Mainz Microntron MAMI," Institut fur Kernphysik, Universitat Mainz, D-55099, Mainz Germany.
Bakhtyari, A. et al., "Horn Resonator Boosts Miniature Free-Electron Laser Power," Applied Physics Letters, May 12, 2003, pp. 3150-3152, vol. 82, No. 19,American Institute of Physics.
Bakhtyari, Dr. Arash, "Gain Mechanism in a Smith-Purcell MicroFEL," Abstract, Department of Physics and Astronomy, Dartmouth College.
Bhattacharjee, Sudeep et al., "Folded Waveguide Traveling-Wave Tube Sources for Terahertz Radiation." IEEE Transactions on Plasma Science, vol. 32. No. 3, Jun. 2004, pp. 1002-1014.
Booske, J.H. et al., "Microfabricated TWTs as High Power, Wideband Sources of Thz Radiation".
Brau, C.A. et al., "Gain and Coherent Radiation from a Smith-Purcell Free Electron Laser," Proceedings of the 2004 FEL Conference, pp. 278-281.
Brownell, J.H. et al., "Improved μFEL Performance with Novel Resonator," Jan. 7, 2005, from website: www. frascati.enea.it/thz-bridge/workshop/presentations/Wednesday/We-07-Brownell. ppt.
Brownell, J.H. et al., "The Angular Distribution of the Power Produced by Smith-Purcell Radition," J. Phys. D; Appl. Phys. 1997, pp. 2478-2481, vol. 30, IOP Publishing Ltd., United Kingdom.
Chuang, S.L. et al., "Enhancement of Smith-Purcell Radiation from a Grating with Surface-Plasmon Excitation," Journal of the Optical Society of America, Jun. 1984, pp. 672-676, vol. 1 No. 6, Optical Society of America.
Chuang, S.L. et al., "Smith-Purcell Radiation from a Charge Moving Above a Penetrable Grating," IEEE MTT-S Digest, 1983, pp. 405-406,IEEE.
Far-IR, Sub-MM & MM Detector Technology Workshop list of manuscripts, session 6 2002.
Feltz, W.F. et al., "Near-Continuous Profiling of Temperature, Moisture, and Atmoshperic Stability Using the Atmospheric Emitted Radiance Interferometer (AERI)," Journal of Applied Meterology, May 2003, vol. 42 No. 5, H.W. Wilson Company, pp. 584-597.
Freund, H. P. et al., "Linearized Field Theory of a Smith-Purcell Traveling Wave Tube,"IEEE Transactions on Plasma Science, Jun. 2004, pp. 1015-1027, vo. 32 No. 3, IEEE.
Gallerano, G.P. et al., "Overview of Terahertz Radiation Sources," Proceedings of the 2004 FEL Conference, pp. 216-221.
Goldstein, M. et al., "Demonstration of a Micro Far-Infrared Smith-Purcell Emitter," Applied Physics Letters, Jul. 28, 1997, pp. 452-454, vol. 71 No. 4, American Institute of Physics.
Gover, A. et al., "Angular Radiation Pattern of Smith-Purcell Radiation," Journal of the Optical Society of America, Oct. 1984, pp. 723-728, vol. 1 No. 5, Optical Society of America.
Grishin, Yu. A. et al., "Pulsed Orotron—A New Microwave Source for Submillimeter Pulse High—Field Electron Paramagnetic Resonance Spectrocscopy," Review of Scientific Instruments, Sep. 2004, pp. 2926-2936, vol. 75 No. 9, American Institute of Physics.
Ishizuka, H. et al., "Smith-Purcell Experiment Utilizing a Field-Emitter Array Cathode: Measurements of Radiation," Nuclear Instruments and Methods in Physics Research, 2001, pp. 593-598, A 475, Elsevier Science B.V.
Ishizuka, H. et al., "Smith-Purcell Radiation Experiment Using a Field-Emission Array Cathode," Nuclear Instruments and Methods in Physics Research, 2000, pp. 276-280, A 445, Elsevier Science B.V.
Ives, Lawrence et al., "Development of Backward Wave Oscillators for Terahertz Applications," Terahertz for Military and Security Applications, Proceedings of SPIE vol. 5070 (2003), pp. 71-82.
Ives, R. Lawrence, "IVEC Summary, Session 2, Sources I" 2002.
Jonietz, Erika, "Nano Antenna Gold nanospheres show path to all-optical computing," Technology Review, Dec. 2005/Jan. 2006, p. 32.
Joo, Youngcheol et al., "Air Cooling of IC Chip with Novel Microchannels Monolithically Formed on Chip Front Surface," Cooling and Thermal Design of Electronic Systems (HTD-vol. 319 & EEP-vol 15), International Mechanical Engineering Congress and Exposition, San Francisco, CA, Nov. 1995, pp. 117-121.
Joo, Youngcheol et al., "Fabrication of Monolithic Microchannels for IC Chip Cooling," 1995, Mechanical, Aerospace and Nuclear Engineering Department, University of California at Los Angeles.
Jung, K.B. et al., "Patterning of Cu, Co, Fe, and Ag for magnetic nanostructures," J. Vac. Sci. Technol. A 15(3), May/Jun. 1997, pp. 1780-1784.
Kapp, Oscar H. et al., "Modification of a Scanning Electron Microscope to Produce Smith-Purcell Radiation," Review of Scientific Instruments, Nov. 2004, pp. 4732-4741, vol. 75 No. 11, American Institute of Physics.
Kiener, C. et al., "Investigation of the Mean Free Path of Hot Electrons in GaAs/AlGaAs Heterostructures," Semicond. Sci. Technol., 1994, pp. 193-197, vol. 9, IOP Publishing Ltd., United Kingdom.
Kim, Shang Hoon, "Quantum Mechanical Theory of Free-Electron Two-Quantum Stark Emission Driven by Transverse Motion," Journal of the Physical Society of Japan, Aug. 1993, Vol. 62 No. 8, pp. 2528-2532.
Korbly, S. E. et al., "Progress on a Smith-Purcell Radiation Bunch Length Diagnostic," Plasma Science and Fusion Center, MIT, Cambridge, MA.
Kormann, T. et al., "A Photoelectron Source for the Study of Smith-Purcell Radiation".
Kube, G. et al., "Observation of Optical Smith-Purcell Radiation at an Electron Beam Energy of 855 MeV," Physical Review E, May 8, 2002, vol. 65, The American Physical Society, pp. 056501-1-056501-15.
Liu, Chuan Sheng, et al., "Stimulated Coherent Smith-Purcell Radiation from a Metallic Grating," IEEE Journal of Quantum Electronics, Oct. 1999, pp. 1386-1389, vol. 35, No. 10, IEEE.
Manohara, Harish et al., "Field Emission Testing of Carbon Nanotubes for THz Frequencey Vacuum Microtube Sources." Abstract. Dec. 2003. from SPIEWeb.
Manohara, Harish M. et al., "Design and Fabrication of a THz Nanoklystron".
Manohara, Harish M. et al., "Design and Fabrication of a THz Nanoklystron" (www.sofia.usrs.edu/det_workshop/ posters/session 3/3-43manohara_poster.pdf), PowerPoint Presentation.
McDaniel, James C. et al., "Smith-Purcell Radiation in the High Conductivity and Plasma Frequency Limits," Applied Optics, Nov. 15, 1989, pp. 4924-4929, vol. 28, No. 22, Optical Society of America.
Meyer, Stephan, "Far IR, Sub-MM & MM Detector Technology Workshop Summary," Oct. 2002. (may date the Manohara documents).
Nguyen, Phucanh et al., "Novel technique to patter silver using CF4 and CF4/O2 glow discharges," J. Vac. Sci. Technol. B 19(1), Jan./Feb. 2001, American Vacuum Society, pp. 158-165.
Nguyen, Phucanh et al., "Reactive ion etch of patterned and blanket silver thin films in Cl2/O2 and O2 glow discharges," J. Vac. Sci, Technol. B. 17 (5), Sep./Oct. 1999, American Vacuum Society, pp. 2204-2209.
Ohtaka, Kazuo, "Smith-Purcell Radiation from Metallic and Dielectric Photonic Crystals," Center for Frontier Science, pp. 272-273, Chiba University, 1-33 Yayoi, Inage-ku, Chiba-shi, Japan.
Phototonics Research, "Surface-Plasmon-Enhanced Random Laser Demonstrated," Phototonics Spectra, Feb. 2005, pp. 112-113.
Platt, C.L. et al., "A New Resonator Design for Smith-Purcell Free Electron Lasers," 6Q19, p. 296.
Potylitsin, A.P., "Resonant Diffraction Radiation and Smith-Purcell Effect," (Abstract), arXiv: physics/9803043 v2 Apr. 13, 1998.
Potylitsyn, A.P., "Resonant Diffraction Radiation and Smith-Purcell Effect," Physics Letters A, Feb. 2, 1998, pp. 112-116, A 238, Elsevier Science B.V.

Savilov, Andrey V., "Stimulated Wave Scattering in the Smith-Purcell FEL," IEEE Transactions on Plasma Science, Oct. 2001, pp. 820-823, vol. 29, No. 5, IEEE.

Schachter, Levi et al., "Smtih-Purcell Oscillator in an Exponential Gain Regime," Journal of Applied Physics, Apr. 15, 1989, pp. 3267-3269, vol. 65 No. 8, American Institute of Physics.

Schachter, Levi, "Influence of the Guiding Magnetic Field on the Performance of a Smith-Purcell Amplifier Operating in the Weak Compton Regime," Journal of the Optical Society of America, May 1990, pp. 873-876, vol. 7 No. 5, Optical Society of America.

Schachter, Levi, " The Influence of the Guided Magnetic Field on the Performance of a Smith-Purcell Amplifier Operating in the Strong Compton Regime," Journal of Applied Physics, Apr. 15, 1990, pp. 3582-3592, vol. 67 No. 8, American Institute of Physics.

Shih, I. et al., "Experimental Investigations of Smith-Purcell Radiation," Journal of the Optical Society of America, Mar. 1990, pp. 351-356, vol. 7, No. 3, Optical Society of America.

Shih, I. et al., "Measurements of Smith-Purcell Radiation," Journal of the Optical Society of America, Mar. 1990, pp. 345-350, vol. 7 No. 3, Optical Society of America.

Swartz, J.C. et al., "THz-FIR Grating Coupled Radiation Source," Plasma Science, 1998. 1D02, p. 126.

Temkin, Richard, "Scanning with Ease Through the Far Infrared," Science, New Series, May 8, 1998, p. 854, vol. 280, No. 5365, American Association for the Advancement of Science.

Walsh, J.E., et al., 1999. From website: http://www.ieee.org/organizations/pubs/newsletters/leos/feb99/hot2.htm.

Wentworth, Stuart M. et al., "Far-Infrared Composite Microbolometers," IEEE MTT-S Digest, 1990, pp. 1309-1310.

Yamamoto, N. et al., "Photon Emission From Silver Particles Induced by a Hig-Energy Electron Beam," Physical Review B, Nov. 6, 2001, pp. 205419-1-205419-9, vol. 64, The American Physical Society.

Yokoo, K. et al., "Smith-Purcell Radiation at Optical Wavelength Using a Field-Emitter Array," Technical Digest of IVMC, 2003, pp. 77-78.

Zeng, Yuxiao et al., "Processing and encapsulation of silver patterns by using reactive ion etch and ammonia anneal," Materials Chemistry and Physics 66, 2000, pp. 77-82.

* cited by examiner

MULTI-COLOR

MULTI-COLOR

RESONANT STRUCTURE-BASED DISPLAY

CROSS-REFERENCE TO RELATED APPLICATIONS

The present invention is related to the following co-pending U.S. patent applications: (1) U.S. patent application Ser. No. 11/238,991, filed Sep. 30, 2005, entitled "Ultra-Small Resonating Charged Particle Beam Modulator"; (2) U.S. patent application Ser. No. 10/917,511, filed on Aug. 13, 2004, entitled "Patterning Thin Metal Film by Dry Reactive Ion Etching"; (3) U.S. application Ser. No. 11/203,407, filed on Aug. 15, 2005, entitled "Method Of Patterning Ultra-Small Structures"; (4) U.S. application Ser. No. 11/243,476, filed on Oct. 5, 2005, entitled "Structures And Methods For Coupling Energy From An Electromagnetic Wave"; (5) U.S. application Ser. No. 11/243,477, filed on Oct. 5, 2005, entitled "Electron beam induced resonance,", (6) U.S. application Ser. No. 11/418,096, entitled "Selectable Frequency Light Emitter," filed on even date herewith; (7) U.S. application Ser. No. 11/325,571, entitled "Switching Micro-Resonant Structures By Modulating A Beam Of Charged Particles," filed on even date herewith; and (8) U.S. application Ser. No. 11/325,534, entitled "Switching Micro-Resonant Structures Using At Least One Director," filed on even date herewith, which are all commonly owned with the present application, the entire contents of each of which are incorporated herein by reference.

BACKGROUND OF THE INVENTION

1. Field of the Invention

The present invention is directed to a resonant structure-based display and a method of manufacturing the same, and, in one embodiment, to a display utilizing plural resonant structures per pixel where the resonant structures are excited by a charged particle source such as an electron beam.

2. Discussion of the Background

Known phosphor-based and plasma-based displays utilize a series of red, green and blue elements to produce an image that can be displayed to a user, e.g., as part of a computer display/monitor or the display for an electronics component, such as a television screen. As the density of the display increases, so does the detail of the display. Accordingly, it is desirable to have as small and dense a display as possible.

SUMMARY OF THE INVENTION

It is an object of the present invention to provide a single- or multi-wavelength display that utilizes an innovative resonant structure to produce the images thereof. An exemplary embodiment of such a display can be constructed with a single resonant structure per wavelength per pixel or with multiple resonant structures per wavelength per pixel.

BRIEF DESCRIPTION OF THE DRAWINGS

The following description, given with respect to the attached drawings, may be better understood with reference to the non-limiting examples of the drawings, wherein.

DISCUSSION OF THE PREFERRED EMBODIMENTS

Figure 1:
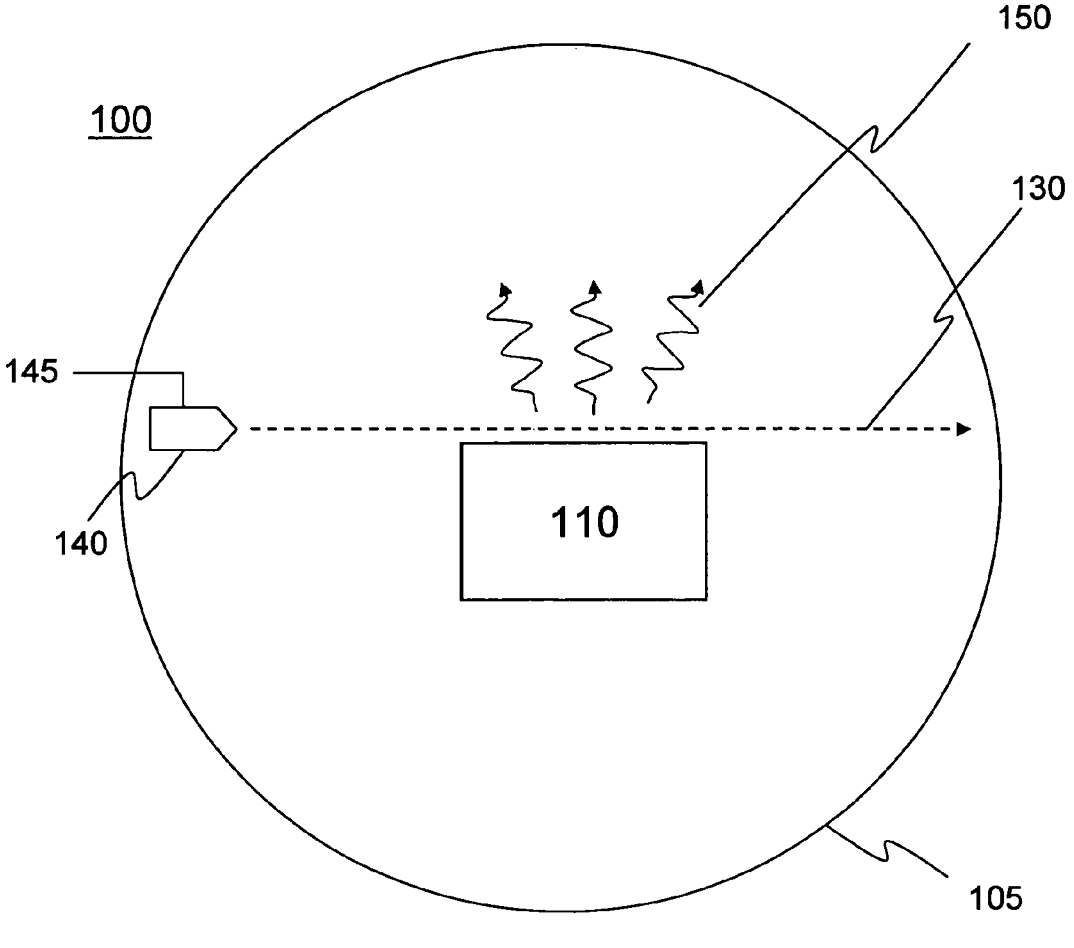
FIG. 1 is a generalized block diagram of a generalized resonant structure and its charged particle source.

Turning to FIG. 1, according to the present invention, a wavelength element 100 on a substrate 105 (such as a semiconductor substrate or a circuit board) can be produced from at least one resonant structure 110 that emits light (such as infrared light, visible light or ultraviolet light or any other electromagnetic radiation (EMR) 150 at a wide range of frequencies, and often at a frequency higher than that of microwave). The EMR 150 is emitted when the resonant structure 110 is exposed to a beam 130 of charged particles ejected from or emitted by a source of charged particles 140. The source 140 is controlled by applying a signal on data input 145. The source 140 can be any desired source of charged particles such as an electron gun, a cathode, an electron source from a scanning electron microscope, etc.

Figure 2A:
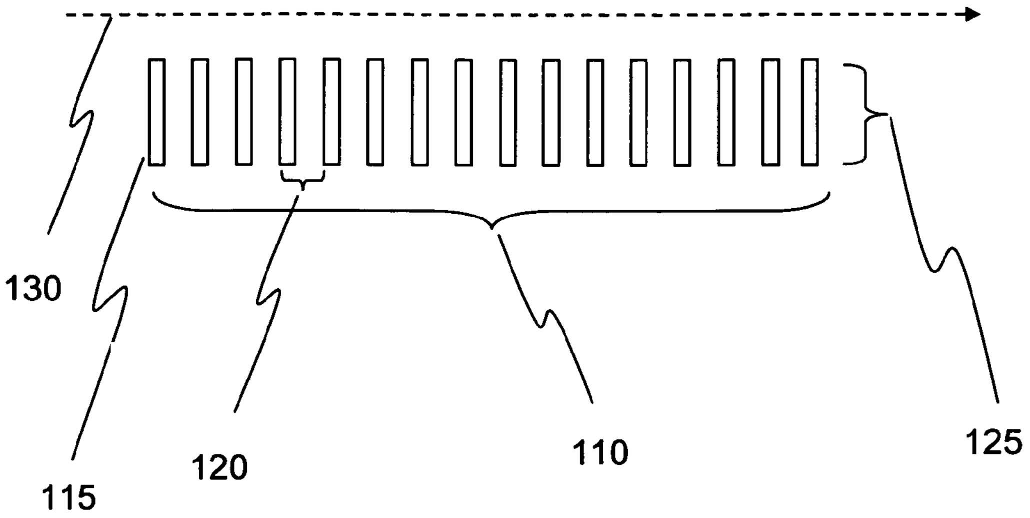
FIG. 2A is a top view of a non-limiting exemplary resonant structure for use with the present invention.

Exemplary resonant structures are illustrated in FIGS. 2A-2H. As shown in FIG. 2A, a resonant structure 110 may comprise a series of fingers 115 which are separated by a spacing 120 measured as the beginning of one finger 115 to the beginning of an adjacent finger 115. The finger 115 has a thickness that takes up a portion of the spacing between fingers 115. The fingers also have a length 125 and a height (not shown). As illustrated, the fingers of FIG. 2A are perpendicular to the beam 130.

Resonant structures 110 are fabricated from resonating material (e.g., from a conductor such as metal (e.g., silver, gold, aluminum and platinum or from an alloy) or from any other material that resonates in the presence of a charged particle beam). Other exemplary resonating materials include carbon nanotubes and high temperature superconductors.

When creating any of the elements 100 according to the present invention, the various resonant structures can be constructed in multiple layers of resonating materials but are preferably constructed in a single layer of resonating material (as described above).

In one single layer embodiment, all the resonant structures 110 of a resonant element 100 are etched or otherwise shaped in the same processing step. In one multi-layer embodiment, the resonant structures 110 of each resonant frequency are etched or otherwise shaped in the same processing step. In yet another multi-layer embodiment, all resonant structures having segments of the same height are etched or otherwise shaped in the same processing step. In yet another embodiment, all of the resonant elements 100 on a substrate 105 are etched or otherwise shaped in the same processing step.

The material need not even be a contiguous layer, but can be a series of resonant elements individually present on a substrate. The materials making up the resonant elements can be produced by a variety of methods, such as by pulsed-plating, depositing, sputtering or etching. Preferred methods for doing so are described in co-pending U.S. application Ser. No. 10/917,571, filed on Aug. 13, 2004, entitled "Patterning Thin Metal Film by Dry Reactive Ion Etching," and in U.S. application Ser. No. 11/203,407, filed on Aug. 15, 2005, entitled "Method Of Patterning Ultra-Small Structures," both of which are commonly owned at the time of filing, and the entire contents of each of which are incorporated herein by reference.

At least in the case of silver, etching does not need to remove the material between segments or posts all the way down to the substrate level, nor does the plating have to place the posts directly on the substrate. Silver posts can be on a silver layer on top of the substrate. In fact, we discovered that, due to various coupling effects, better results are obtained when the silver posts are set on a silver layer, which itself is on the substrate.

Figure 2B:
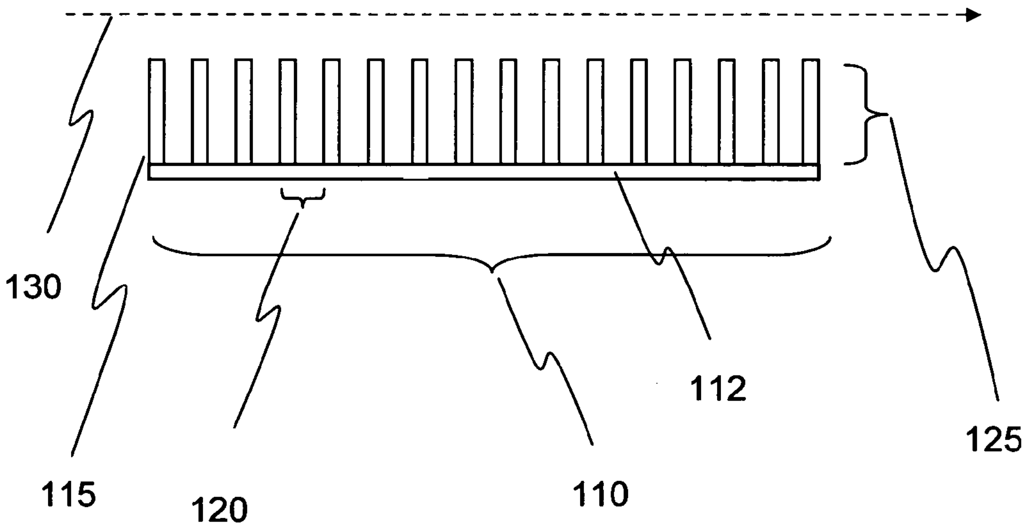
FIG. 2B is a top view of the exemplary resonant structure of FIG. 2A with the addition of a backbone.
Figure 2C:
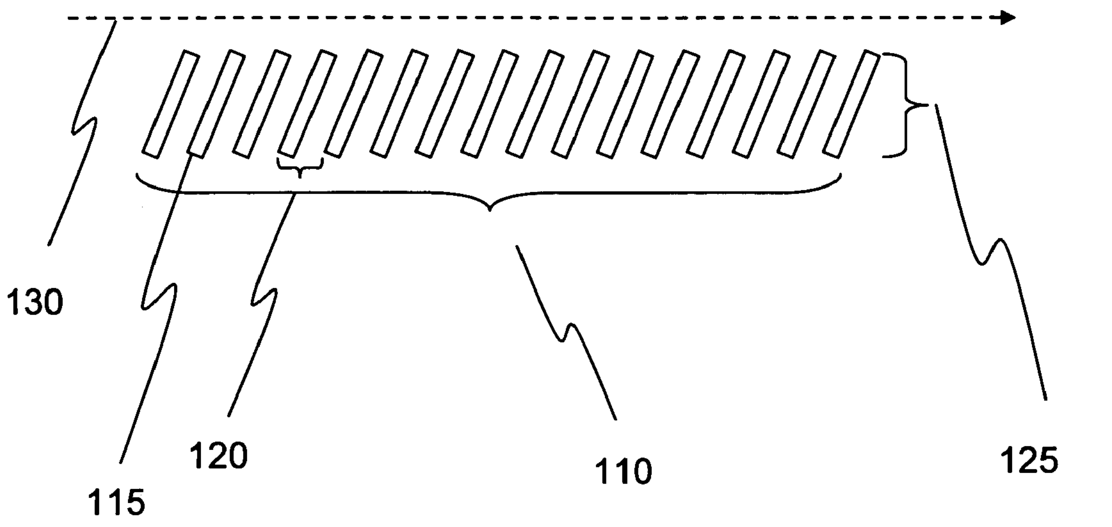
FIGS. 2C-2H are top views of other exemplary resonant structures for use with the present invention.
Figure 2D:
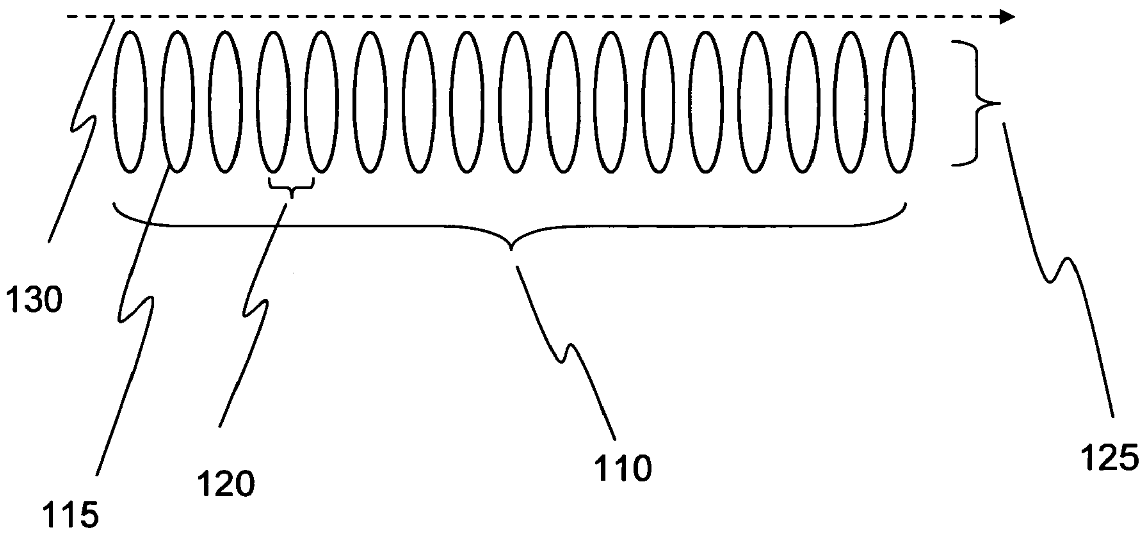
Figure 2E:
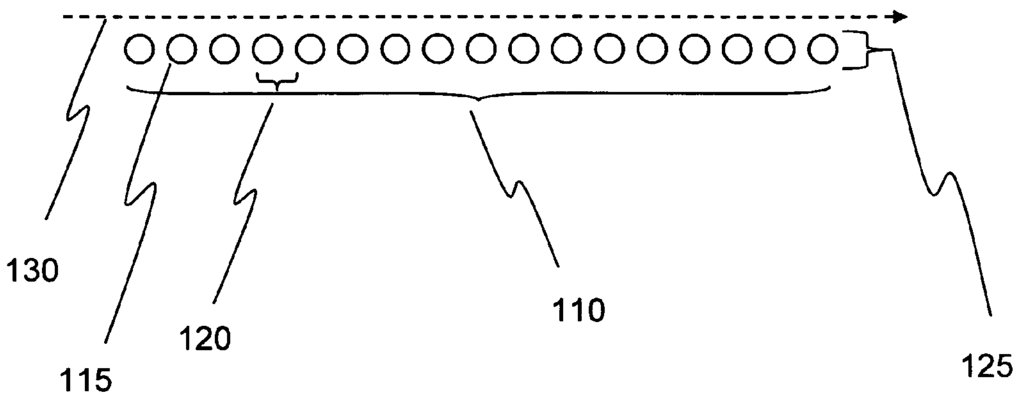
Figure 2F:
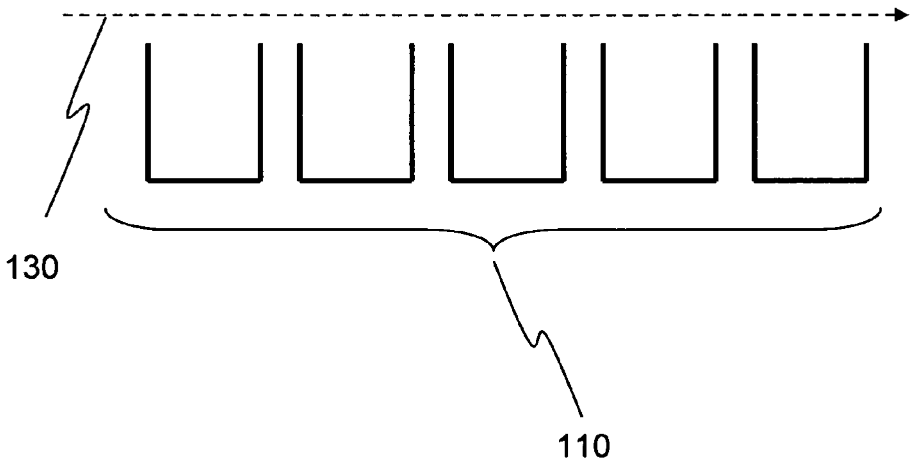
Figure 2G:
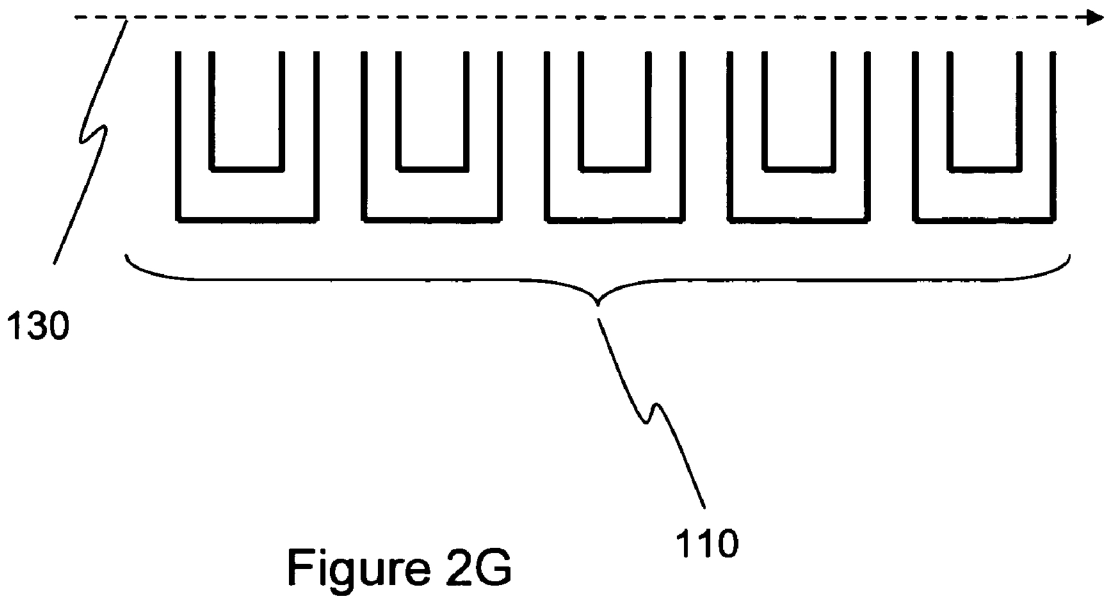
Figure 2H:
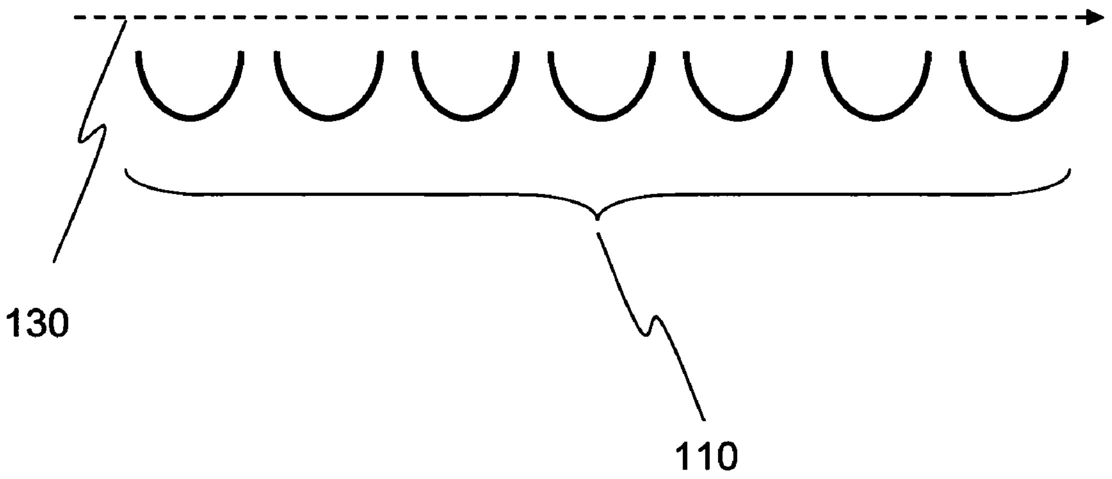

As shown in FIG. 2B, the fingers of the resonant structure 110 can be supplemented with a backbone. The backbone 112 connects the various fingers 115 of the resonant structure 110 forming a comb-like shape on its side. Typically, the backbone 112 would be made of the same material as the rest of the resonant structure 110, but alternate materials may be used. In addition, the backbone 112 may be formed in the same layer or a different layer than the fingers 110. The backbone 112 may also be formed in the same processing step or in a different processing step than the fingers 110. While the remaining figures do not show the use of a backbone 112, it should be appreciated that all other resonant structures described herein can be fabricated with a backbone also.

The shape of the fingers 115R (or posts) may also be shapes other than rectangles, such as simple shapes (e.g., circles, ovals, arcs and squares), complex shapes (e.g., such as semicircles, angled fingers, serpentine structures and embedded structures (i.e., structures with a smaller geometry within a larger geometry, thereby creating more complex resonances)) and those including waveguides or complex cavities. The finger structures of all the various shapes will be collectively referred to herein as "segments." Other exemplary shapes are shown in FIGS. 2C-2H, again with respect to a path of a beam 130. As can be seen at least from FIG. 2C, the axis of symmetry of the segments need not be perpendicular to the path of the beam 130.

Figure 3:
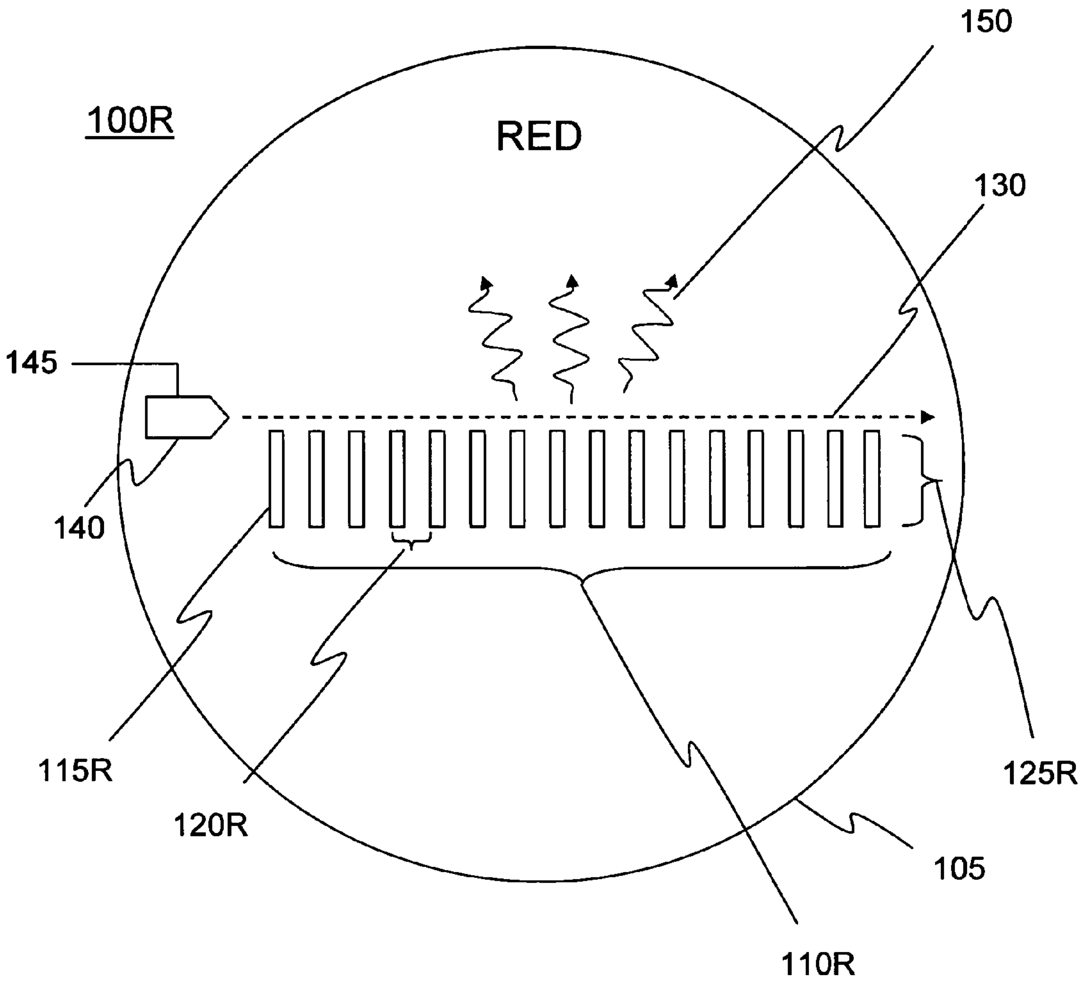
FIG. 3 is a top view of a single wavelength element having a first period and a first "finger" length according to one embodiment of the present invention.
Figure 4:
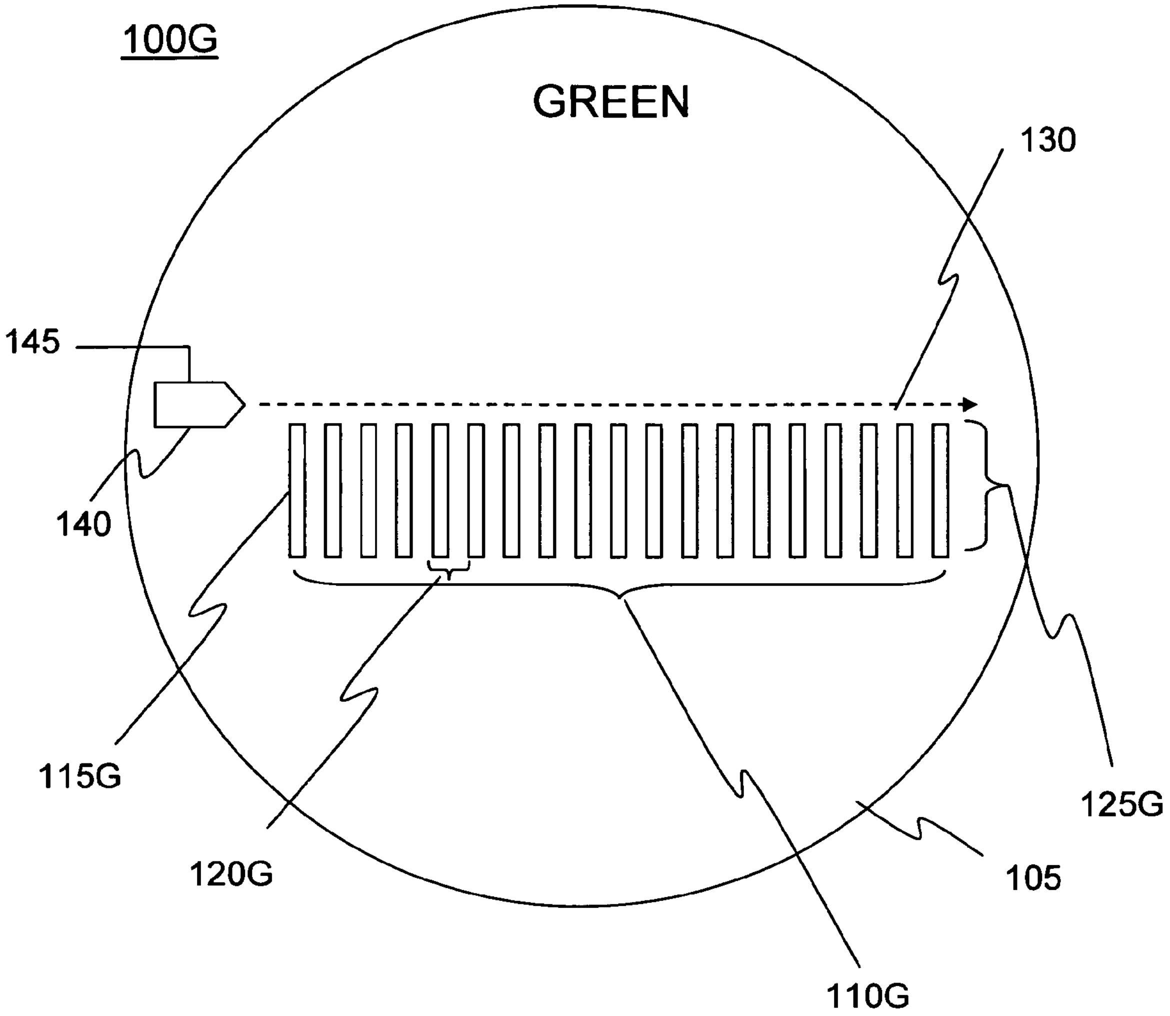
FIG. 4 is a top view of a single wavelength element having a second period and a second "finger" length according to one embodiment of the present invention.
Figure 5:
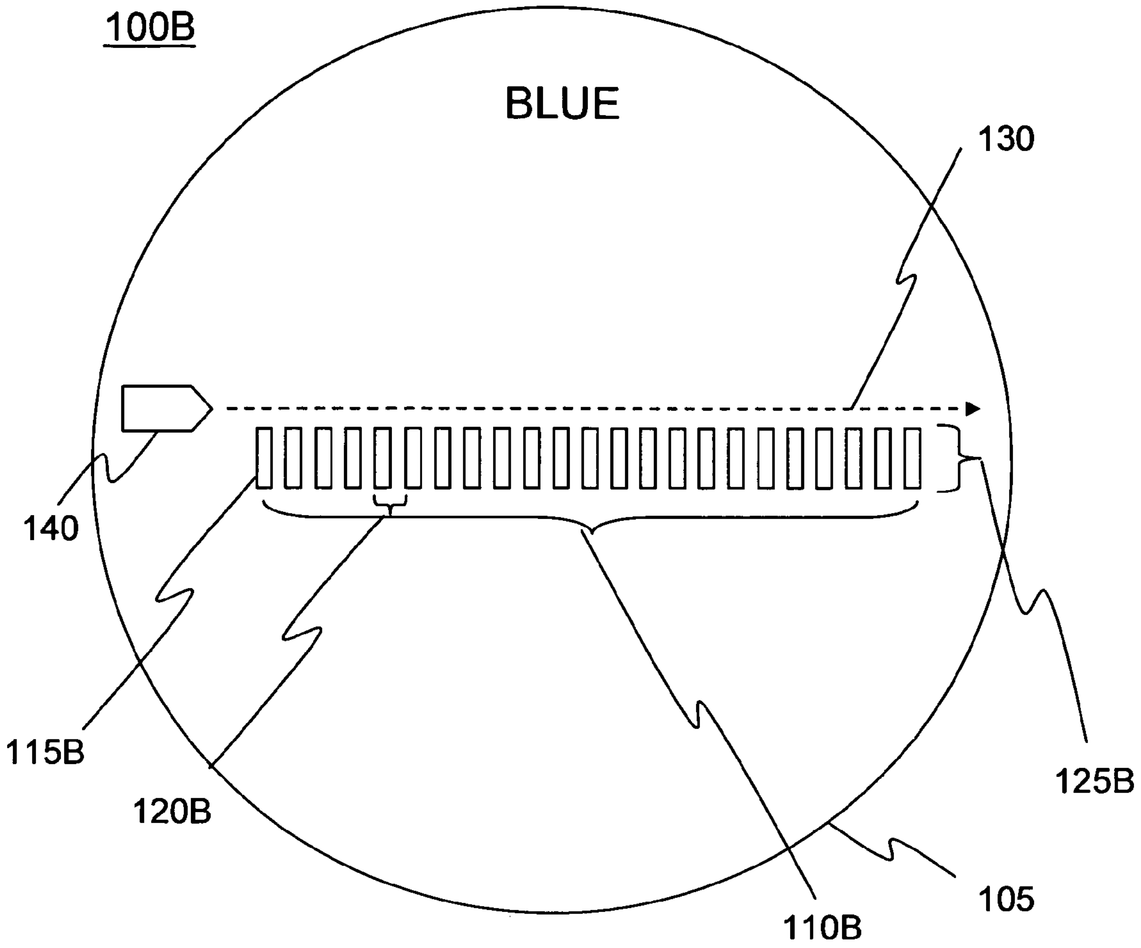
FIG. 5 is a top view of a single wavelength element having a third period and a third "finger" length according to one embodiment of the present invention.

Turning now to specific exemplary resonant elements, in FIG. 3, a wavelength element 100R for producing electromagnetic radiation with a first frequency is shown as having been constructed on a substrate 105. (The illustrated embodiments of FIGS. 3, 4 and 5 are described as producing red, green and blue light in the visible spectrum, respectively. However, the spacings and lengths of the fingers 115R, 115G and 115B of the resonant structures 110R, 110G and 110B, respectively, are for illustrative purposes only and not intended to represent any actual relationship between the period 120 of the fingers, the lengths of the fingers 115 and the frequency of the emitted electromagnetic radiation.) However, the dimensions of exemplary resonant structures are provided in the table below.

| Wavelength | Period 120 | Segment thickness | Height 155 | Length 125 | # of fingers in a row |
|---|---|---|---|---|---|
| Red | 220 nm | 110 nm | 250-400 nm | 100-140 nm | 200-300 |
| Green | 171 nm | 85 nm | 250-400 nm | 180 nm | 200-300 |
| Blue | 158 nm | 78 nm | 250-400 nm | 60-120 nm | 200-300 |

As dimensions (e.g., height and/or length) change, the intensity of the radiation may change as well. Moreover, depending on the dimensions, harmonics (e.g., second and third harmonics) may occur. For post height, length, and width, intensity appears oscillatory in that finding the optimal peak of each mode created the highest output. When operating in the velocity dependent mode (where the finger period depicts the dominant output radiation) the alignment of the geometric modes of the fingers are used to increase the output intensity. However it is seen that there are also radiation components due to geometric mode excitation during this time, but they do not appear to dominate the output. Optimal overall output comes when there is constructive modal alignment in as many axes as possible.

Other dimensions of the posts and cavities can also be swept to improve the intensity. A sweep of the duty cycle of the cavity space width and the post thickness indicates that the cavity space width and period (i.e., the sum of the width of one cavity space width and one post) have relevance to the center frequency of the resultant radiation. That is, the center frequency of resonance is generally determined by the post/space period. By sweeping the geometries, at given electron velocity v and current density, while evaluating the characteristic harmonics during each sweep, one can ascertain a predictable design model and equation set for a particular metal layer type and construction. Each of the dimensions mentioned about can be any value in the nanostructure range, i.e., 1 nm to 1 μm. Within such parameters, a series of posts can be constructed that output substantial EMR in the infrared, visible and ultraviolet portions of the spectrum and which can be optimized based on alterations of the geometry, electron velocity and density, and metal/layer type. It should also be possible to generate EMR of longer wavelengths as well. Unlike a Smith-Purcell device, the resultant radiation from such a structure is intense enough to be visible to the human eye with only 30 nanoamperes of current.

Using the above-described sweeps, one can also find the point of maximum intensity for given posts. Additional options also exist to widen the bandwidth or even have multiple frequency points on a single device. Such options include irregularly shaped posts and spacing, series arrays of non-uniform periods, asymmetrical post orientation, multiple beam configurations, etc.

As shown in FIG. 3, a beam 130 of charged particles (e.g., electrons, or positively or negatively charged ions) is emitted from a source 140 of charged particles under the control of a data input 145. The beam 130 passes close enough to the resonant structure 110R to excite a response from the fingers and their associated cavities (or spaces). The source 140 is turned on when an input signal is received that indicates that the resonant structure 110R is to be excited. When the input signal indicates that the resonant structure 110R is not to be excited, the source 140 is turned off.

The illustrated EMR 150 is intended to denote that, in response to the data input 145 turning on the source 140, a red wavelength is emitted from the resonant structure 110R. In the illustrated embodiment, the beam 130 passes next to the resonant structure 110R which is shaped like a series of rectangular fingers 115R or posts.

The resonant structure 110R is fabricated utilizing any one of a variety of techniques (e.g., semiconductor processing-style techniques such as reactive ion etching, wet etching and pulsed plating) that produce small shaped features.

In response to the beam 130, electromagnetic radiation 150 is emitted therefrom which can be directed to an exterior of the element 110.

As shown in FIG. 4, a green element 100G includes a second source 140 providing a second beam 130 in close proximity to a resonant structure 110G having a set of fingers 115G with a spacing 120G, a finger length 125G and a finger height 155G (see FIG. 9) which may be different than the spacing 120R, finger length 125G and finger height 155R of the resonant structure 110R. The finger length 125, finger spacing 120 and finger height 155 may be varied during design time to determine optimal finger lengths 125, finger spacings 120 and finger heights 155 to be used in the desired application.

As shown in FIG. 5, a blue element 100B includes a third source 140 providing a third beam 130 in close proximity to a resonant structure 110B having a set of fingers 115B having a spacing 120B, a finger length 125B and a finger height 155B (see FIG. 10) which may be different than the spacing 120R, length 125R and height 155R of the resonant structure 110R and which may be different than the spacing 120G, length 125G and height 155G of the resonant structure 110G.

The cathode sources of electron beams, as one example of the charged particle beam, are usually best constructed off of the chip or board onto which the conducting structures are constructed. In such a case, we incorporate an off-site cathode with a deflector, diffractor, or switch to direct one or more electron beams to one or more selected rows of the resonant structures. The result is that the same conductive layer can produce multiple light (or other EMR) frequencies by selectively inducing resonance in one of plural resonant structures that exist on the same substrate 105.

Figure 6A:
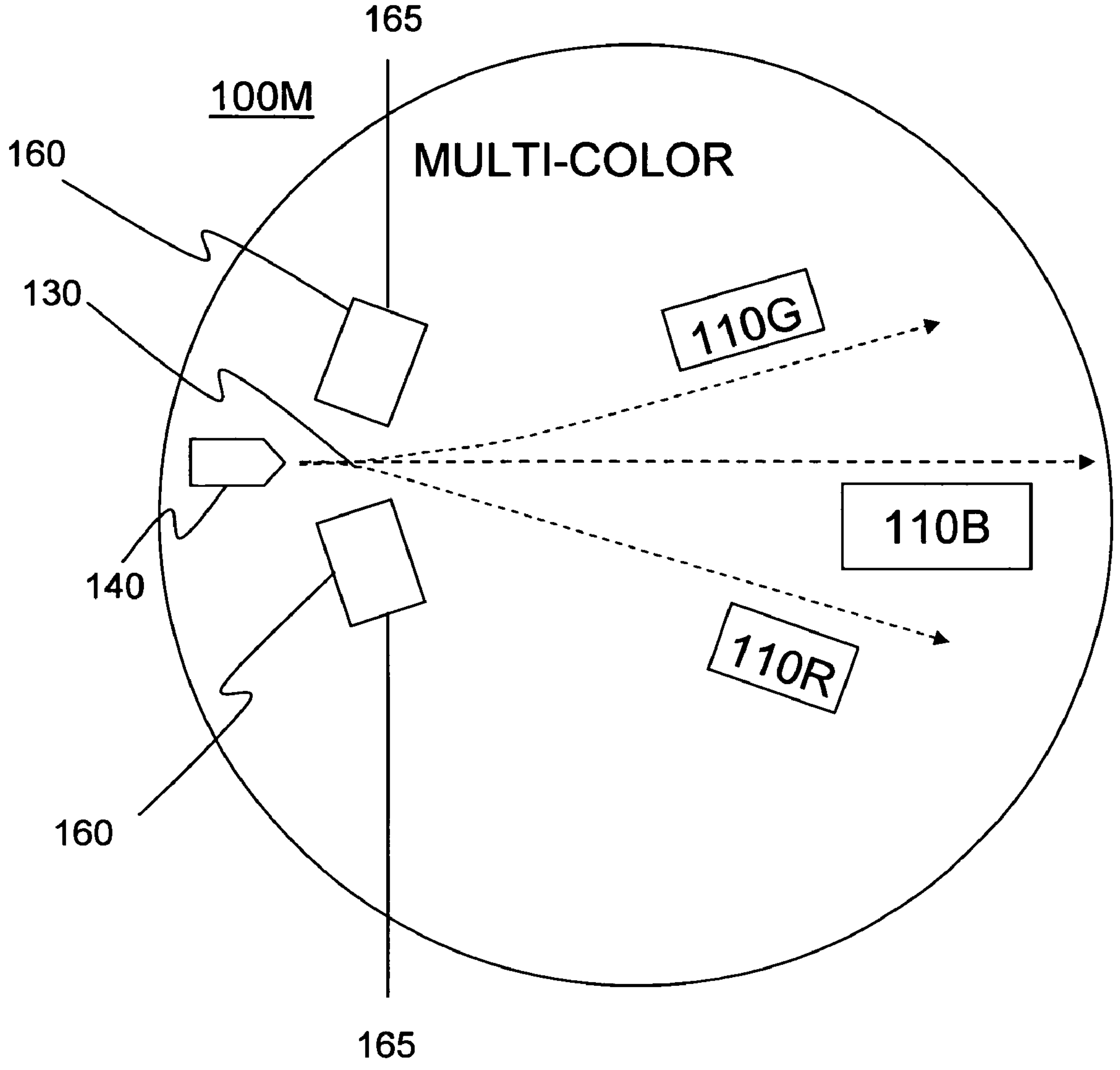
FIG. 6A is a top view of a multi-wavelength element utilizing two deflectors according to one embodiment of the present invention.

In an embodiment shown in FIG. 6A, an element is produced such that plural wavelengths can be produced from a single beam 130. In the embodiment of FIG. 6A, two deflectors 160 are provided which can direct the beam towards a desired resonant structure 110G, 110B or 110R by providing a deflection control voltage on a deflection control terminal 165. One of the two deflectors 160 is charged to make the beam bend in a first direction toward a first resonant structure, and the other of the two deflectors can be charged to make the beam bend in a second direction towards a second resonant structure. Energizing neither of the two deflectors 160 allows the beam 130 to be directed to yet a third of the resonant structures. Deflector plates are known in the art and include, but are not limited to, charged plates to which a voltage differential can be applied and deflectors as are used in cathode-ray tube (CRT) displays.

While FIG. 6A illustrates a single beam 130 interacting with three resonant structures, in alternate embodiments a larger or smaller number of resonant structures can be utilized in the multi-wavelength element 100M. For example, utilizing only two resonant structures 110G and 110B ensures that the beam does not pass over or through a resonant structure as it would when bending toward 110R if the beam 130 were left on. However, in one embodiment, the beam 130 is turned off while the deflector(s) is/are charged to provide the desired deflection and then the beam 130 is turned back on again.

Figure 6B:
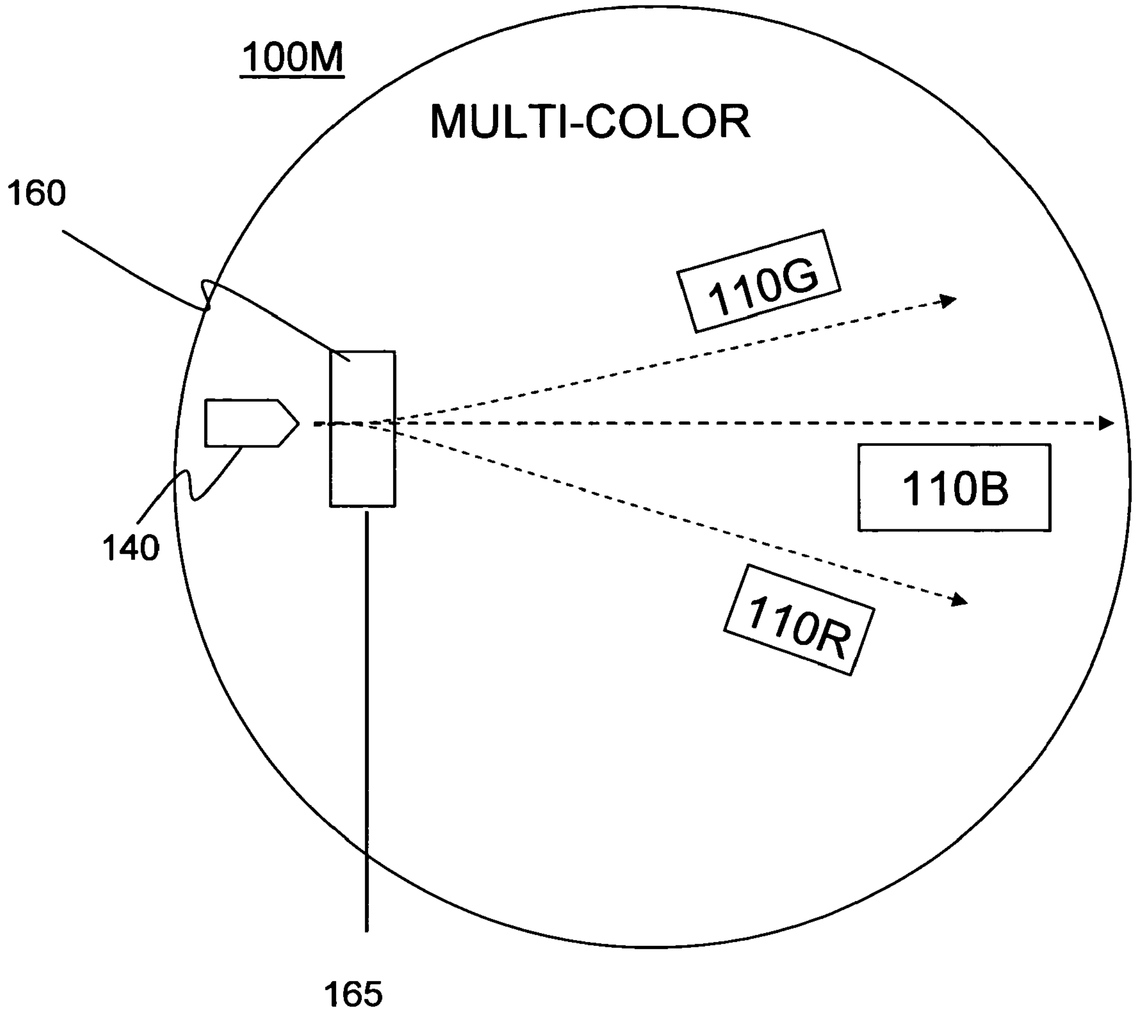
FIG. 6B is a top view of a multi-wavelength element utilizing a single, integrated deflector according to one embodiment of the present invention.
Figure 6C:
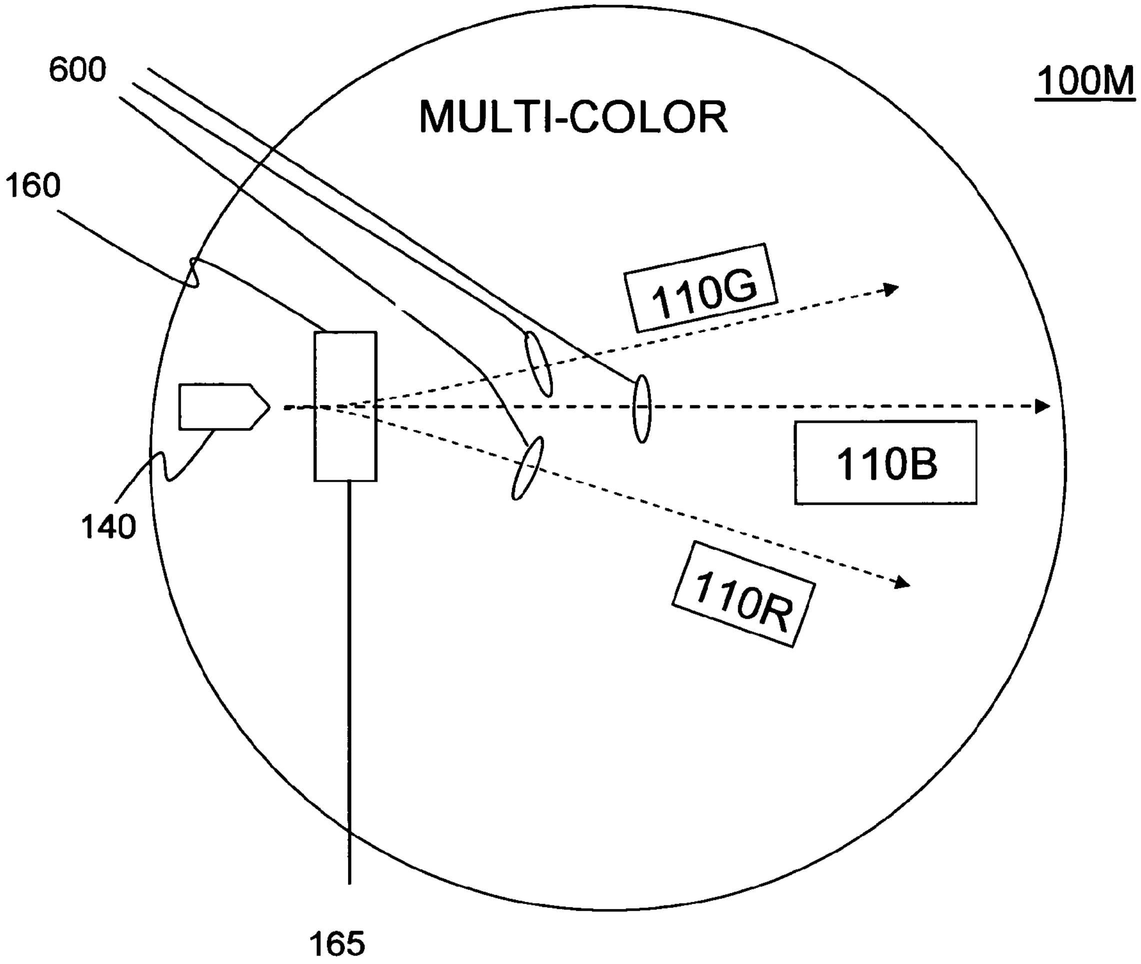
FIG. 6C is a top view of a multi-wavelength element utilizing a single, integrated deflector and focusing charged particle optical elements according to one embodiment of the present invention.

In yet another embodiment illustrated in FIG. 6B, the multi-wavelength structure 100M of FIG. 6A is modified to utilize a single deflector 160 with sides that can be individually energized such that the beam 130 can be deflected toward the appropriate resonant structure. The multi-wavelength element 100M of FIG. 6C also includes (as can any embodiment described herein) a series of focusing charged particle optical elements 600 in front of the resonant structures 110R, 110G and 110B.

Figure 6D:
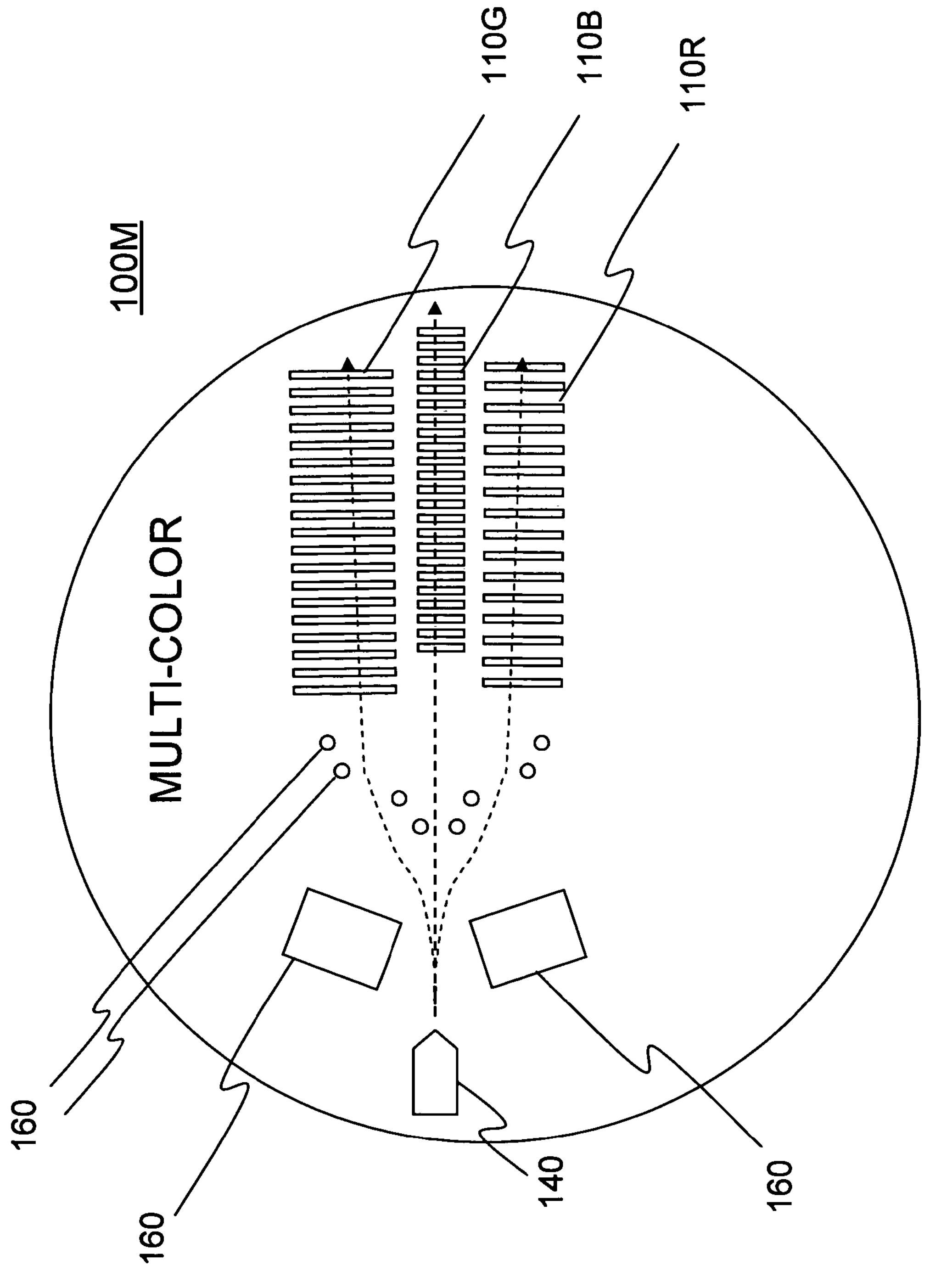
FIG. 6D is a top view of a multi-wavelength element utilizing plural deflectors along various points in the path of the beam according to one embodiment of the present invention.

In yet another embodiment illustrated in FIG. 6D, the multi-wavelength structure 100M of FIG. 6A is modified to utilize additional deflectors 160 at various points along the path of the beam 130. Additionally, the structure of FIG. 6D has been altered to utilize a beam that passes over, rather than next to, the resonant structures 110R, 110G and 110B.

Figure 7:
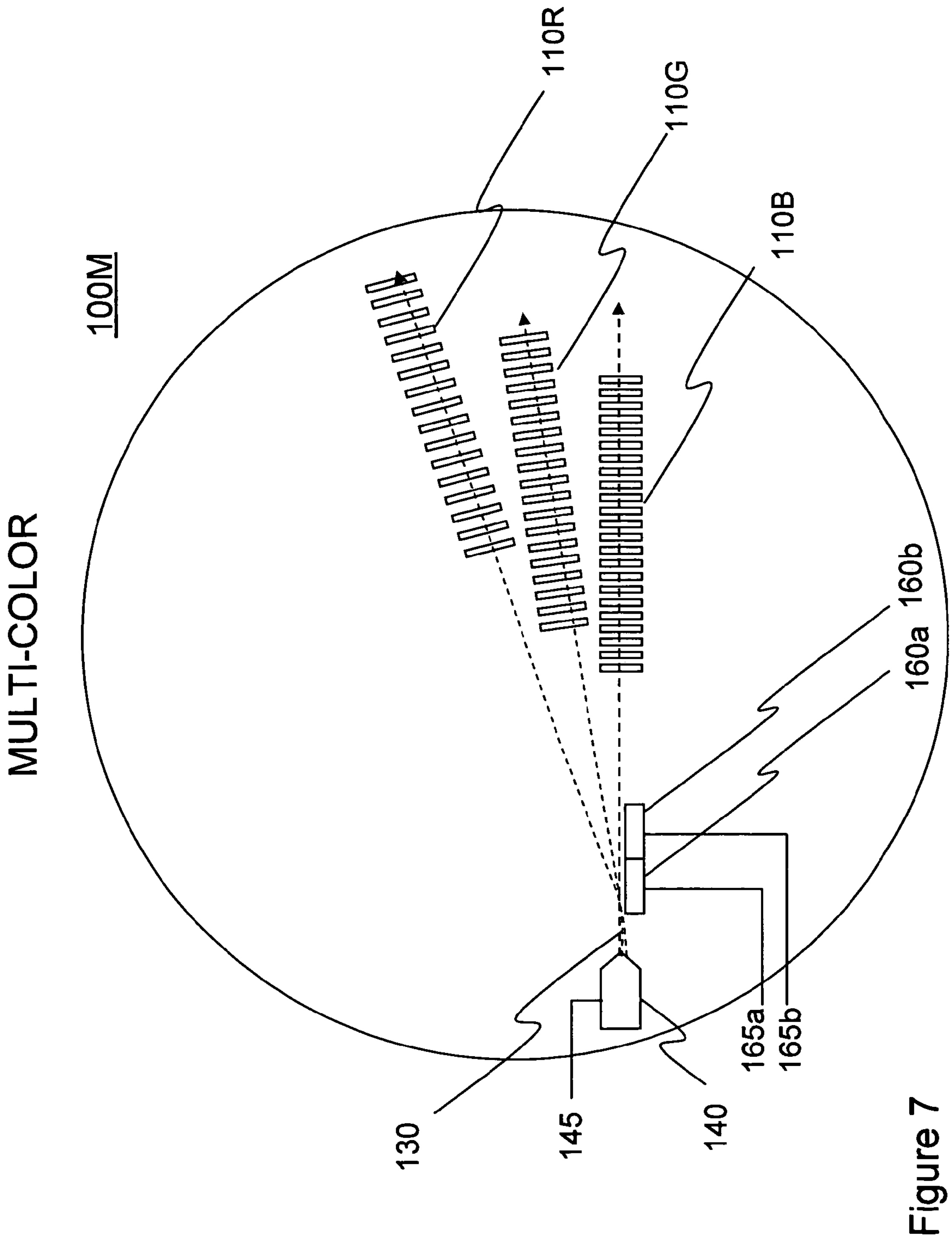
FIG. 7 is a top view of a multi-wavelength element utilizing two serial deflectors according to one embodiment of the present invention.

Alternatively, as shown in FIG. 7, rather than utilize parallel deflectors (e.g., as in FIG. 6A), a set of at least two deflectors 160*a,b* may be utilized in series. Each of the deflectors includes a deflection control terminal 165 for controlling whether it should aid in the deflection of the beam 130. For example, with neither of deflectors 160*a,b* energized, the beam 130 is not deflected, and the resonant structure 110B is excited. When one of the deflectors 160*a,b* is energized but not the other, then the beam 130 is deflected towards and excites resonant structure 110G. When both of the deflectors 160*a,b* are energized, then the beam 130 is deflected towards and excites resonant structure 110R. The number of resonant structures could be increased by providing greater amounts of beam deflection, either by adding additional deflectors 160 or by providing variable amounts of deflection under the control of the deflection control terminal 165.

Alternatively, "directors" other than the deflectors 160 can be used to direct/deflect the electron beam 130 emitted from the source 140 toward any one of the resonant structures 110 discussed herein. Directors 160 can include any one or a combination of a deflector 160, a diffractor, and an optical structure (e.g., switch) that generates the necessary fields.

Figure 8:
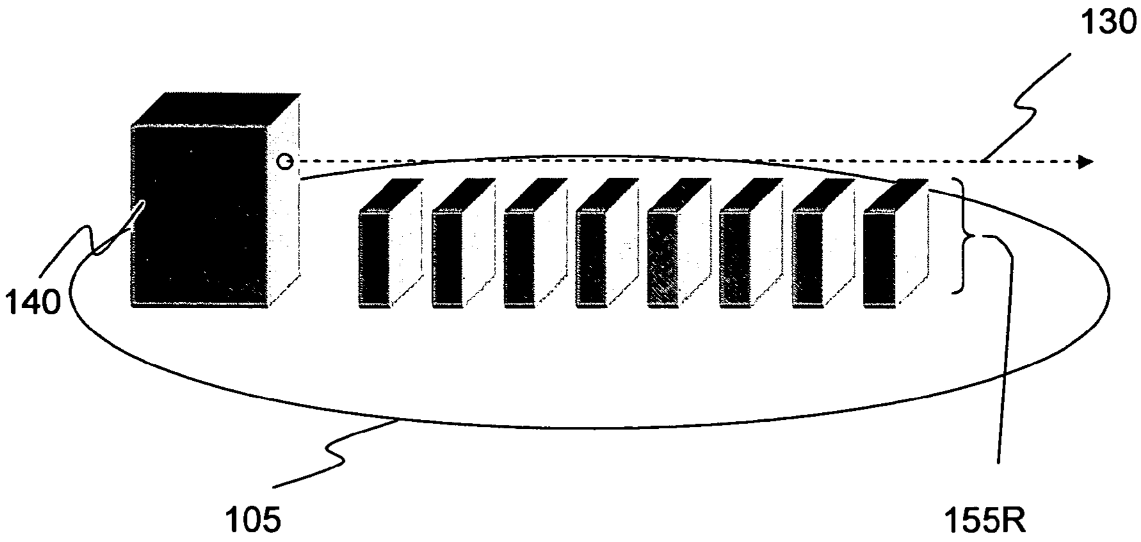
FIG. 8 is a perspective view of a single wavelength element having a first period and a first resonant frequency or "finger" length according to one embodiment of the present invention.
Figure 9:
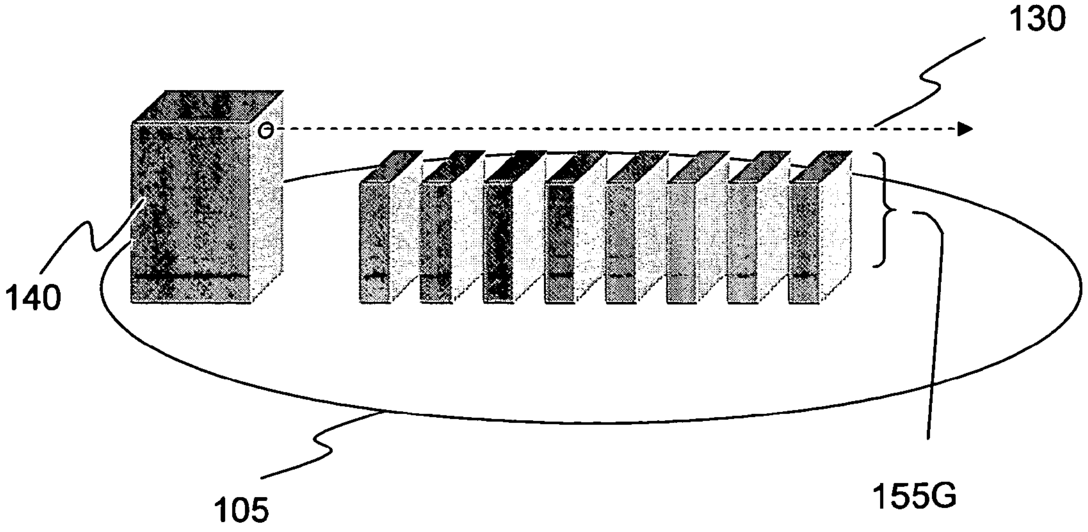
FIG. 9 is a perspective view of a single wavelength element having a second period and a second "finger" length according to one embodiment of the present invention.
Figure 10:
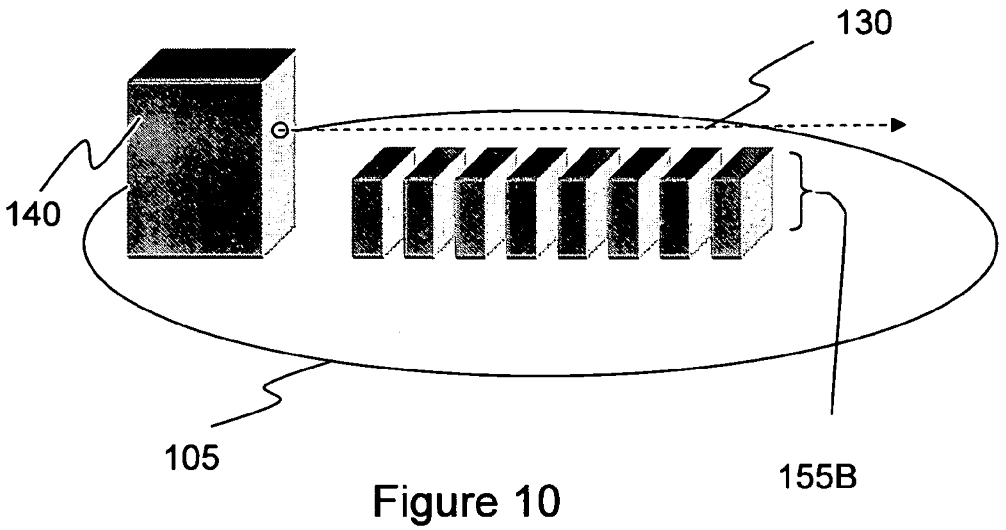
FIG. 10 is a perspective view of a single wavelength element having a third period and a third "finger" length according to one embodiment of the present invention.

While many of the above embodiments have been discussed with respect to resonant structures having beams 130 passing next to them, such a configuration is not required. Instead, the beam 130 from the source 140 may be passed over top of the resonant structures. FIGS. 8, 9 and 10 illustrate a variety of finger lengths, spacings and heights to illustrate that a variety of EMR 150 frequencies can be selectively produced according to this embodiment as well.

Figure 11:
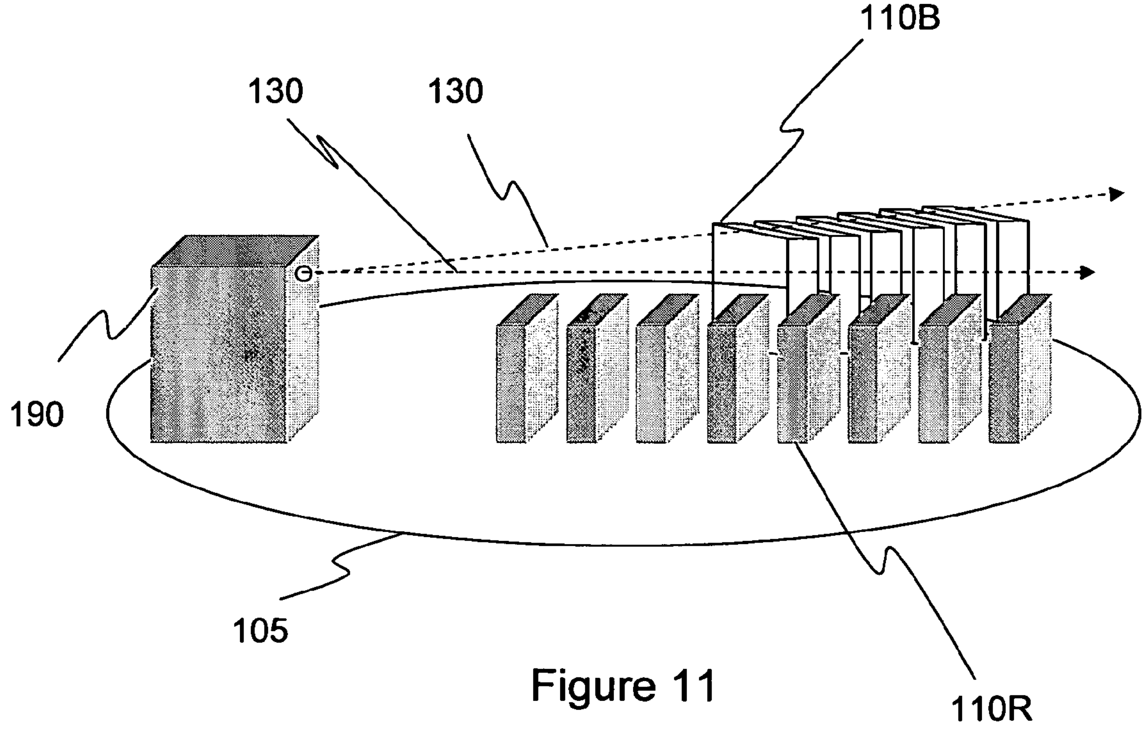
FIG. 11 is a perspective view of a portion of a multi-wavelength element having wavelength elements with different periods and "finger" lengths.

Furthermore, as shown in FIG. 11, the resonant structures of FIGS. 8-10 can be modified to utilize a single source 190 which includes a deflector therein. However, as with the embodiments of FIGS. 6A-7, the deflectors 160 can be separate from the charged particle source 140 as well without departing from the present invention. As shown in FIG. 11, fingers of different spacings and potentially different lengths and heights are provided in close proximity to each other. To activate the resonant structure 110R, the beam 130 is allowed to pass out of the source 190 undeflected. To activate the resonant structure 110B, the beam 130 is deflected after being generated in the source 190. (The third resonant structure for the third wavelength element has been omitted for clarity.)

Figure 12:
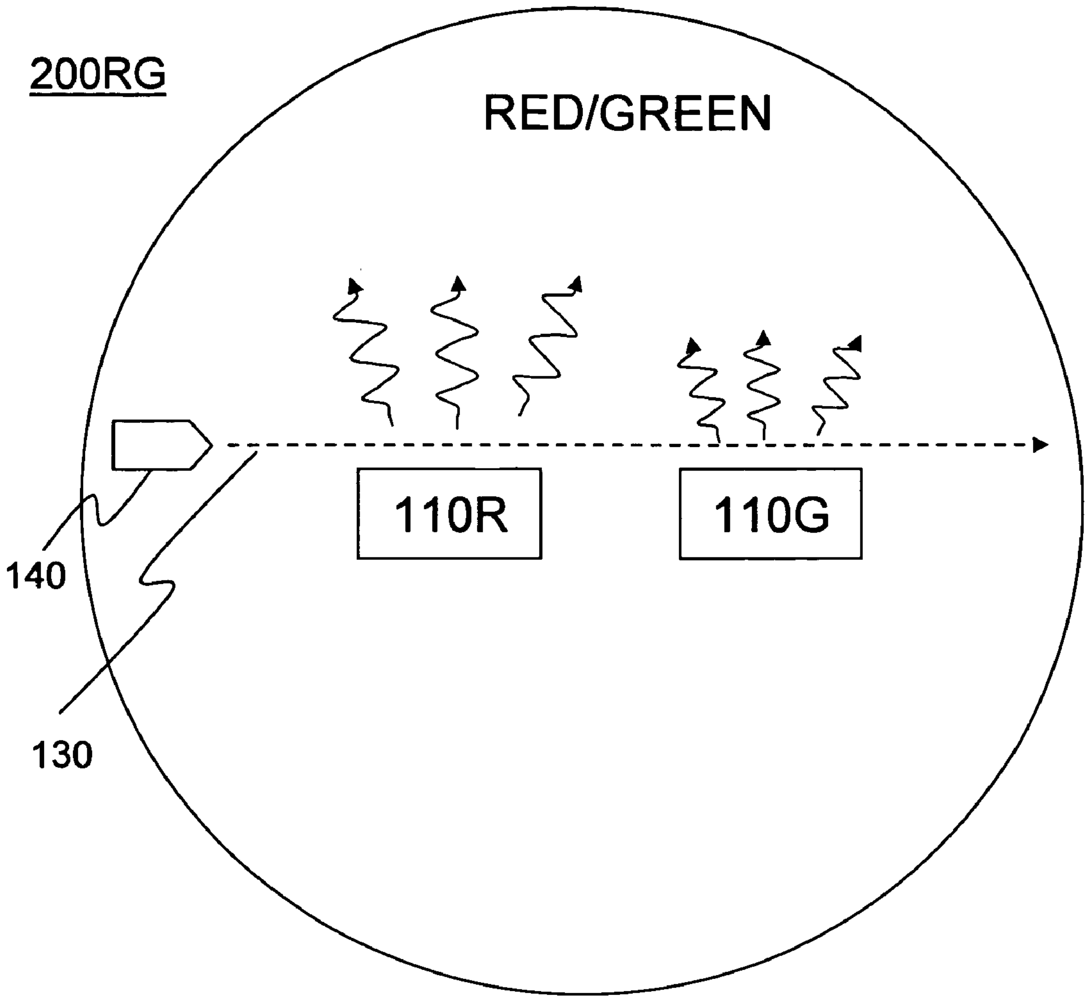
FIG. 12 is a top view of a multi-wavelength element according to one embodiment of the present invention.

While the above elements have been described with reference to resonant structures 110 that have a single resonant structure along any beam trajectory, as shown in FIG. 12, it is possible to utilize wavelength elements 200RG that include plural resonant structures in series (e.g., with multiple finger spacings and one or more finger lengths and finger heights per element). In such a configuration, one may obtain a mix of wavelengths if this is desired. At least two resonant structures in series can either be the same type of resonant structure (e.g., all of the type shown in FIG. 2A) or may be of different types (e.g., in an exemplary embodiment with three resonant structures, at least one of FIG. 2A, at least one of FIG. 2C, at least one of FIG. 2H, but none of the others).

Figure 13:
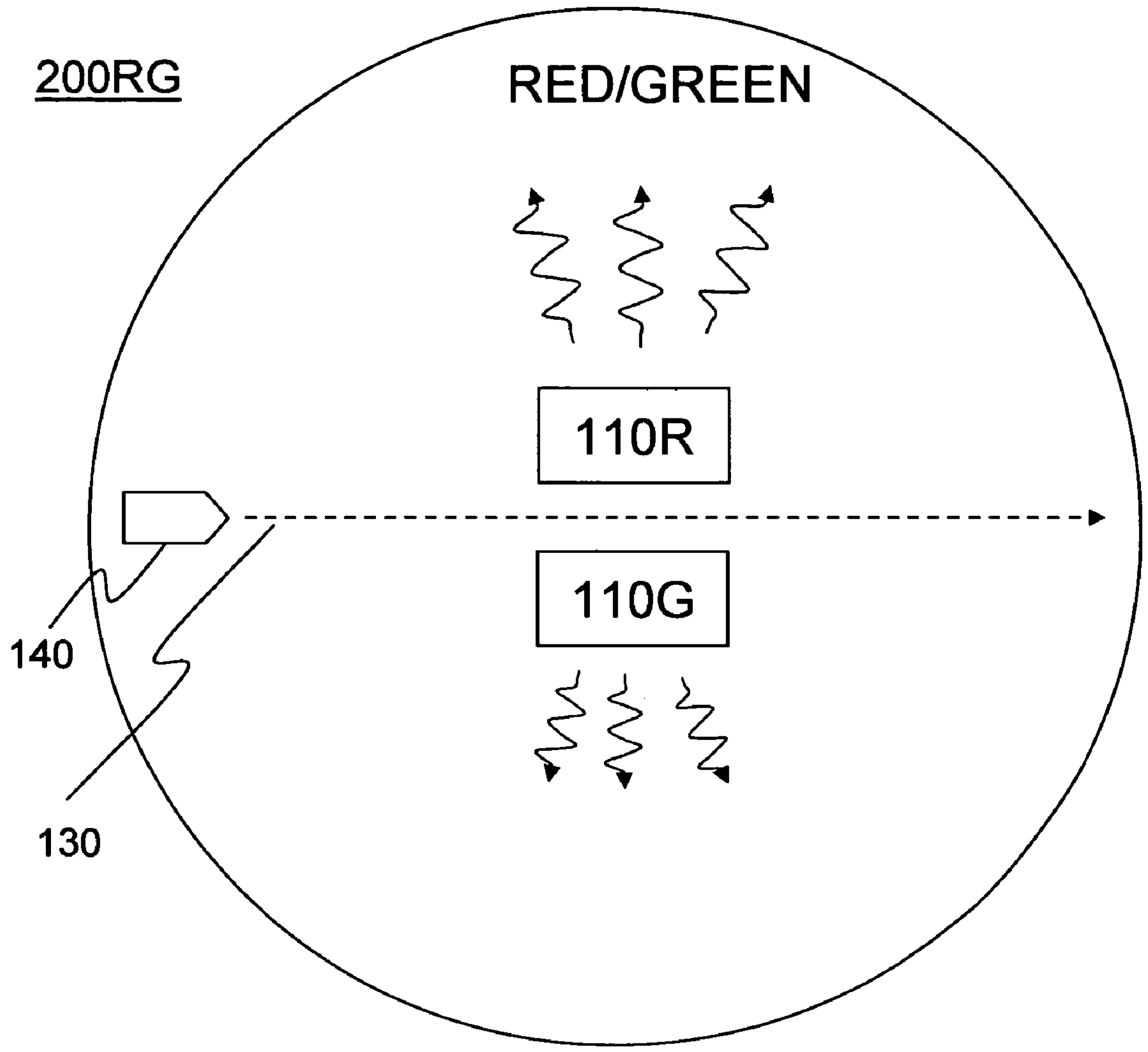
FIG. 13 is a top view of a multi-wavelength element according to another embodiment of the present invention.

Alternatively, as shown in FIG. 13, a single charged particle beam 130 (e.g., electron beam) may excite two resonant structures 110R and 110G in parallel. As would be appreciated by one of ordinary skill from this disclosure, the wavelengths need not correspond to red and green but may instead be any wavelength pairing utilizing the structure of FIG. 13.

It is possible to alter the intensity of emissions from resonant structures using a variety of techniques. For example, the charged particle density making up the beam 130 can be varied to increase or decrease intensity, as needed. Moreover, the speed that the charged particles pass next to or over the resonant structures can be varied to alter intensity as well.

Alternatively, by decreasing the distance between the beam 130 and a resonant structure (without hitting the resonant structure), the intensity of the emission from the resonant structure is increased. In the embodiments of FIGS. 3-7, this would be achieved by bringing the beam 130 closer to the side of the resonant structure. For FIGS. 8-10, this would be achieved by lowering the beam 130. Conversely, by increasing the distance between the beam 130 and a resonant structure, the intensity of the emission from the resonant structure is decreased.

Figure 14:
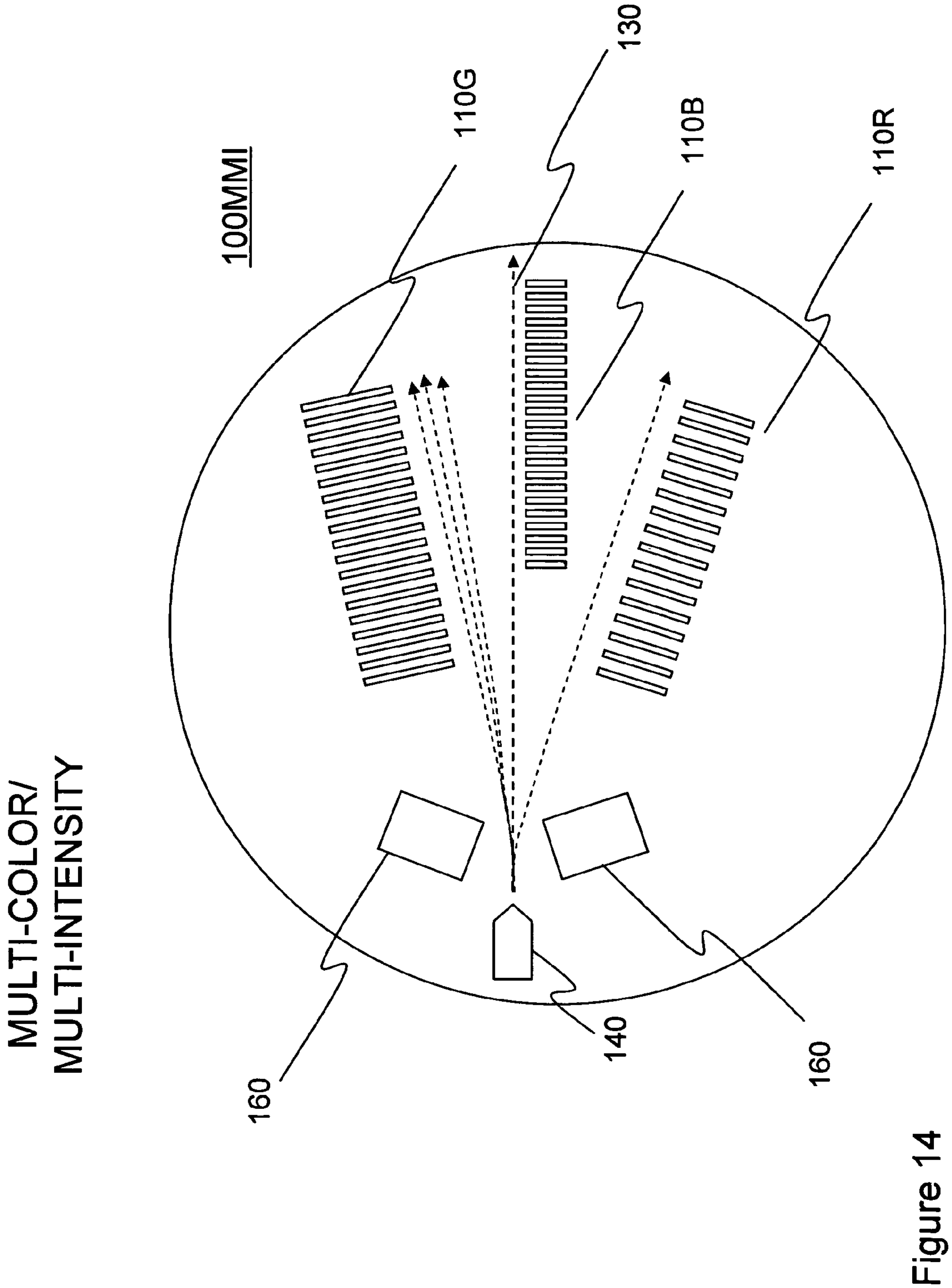
FIG. 14 is a top view of a multi-wavelength element utilizing two deflectors with variable amounts of deflection according to one embodiment of the present invention.

Turning to the structure of FIG. 14, it is possible to utilize at least one deflector 160 to vary the amount of coupling between the beam 130 and the resonant structures 110. As illustrated, the beam 130 can be positioned at three different distances away from the resonant structures 110. Thus, as illustrated at least three different intensities are possible for the green resonant structure, and similar intensities would be available for the red and green resonant structures. However, in practice a much larger number of positions (and corresponding intensities) would be used. For example, by specifying an 8-bit color component, one of 256 different positions would be selected for the position of the beam 130 when in proximity to the resonant structure of that color. Since the resonant structures for different may have different responses to the proximity of the beam, the deflectors are preferably controlled by a translation table or circuit that converts the desired intensity to a deflection voltage (either linearly or non-linearly).

Figure 15:
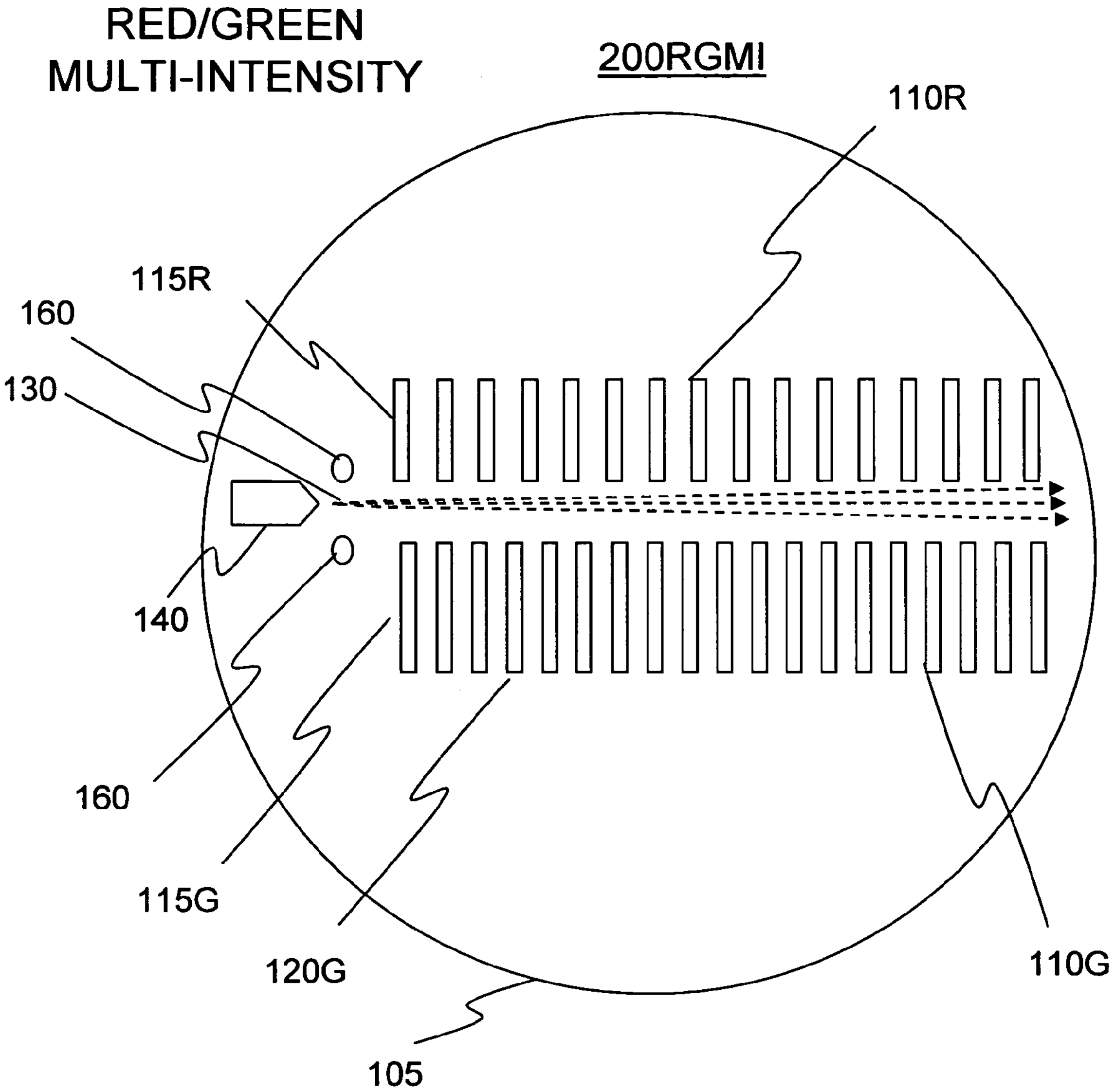
FIG. 15 is a top view of a multi-wavelength element utilizing two deflectors according to another embodiment of the present invention.

Moreover, as shown in FIG. 15, the structure of FIG. 13 may be supplemented with at least one deflector 160 which temporarily positions the beam 130 closer to one of the two structures 110R and 110G as desired. By modifying the path of the beam 130 to become closer to the resonant structures 110R and farther away from the resonant structure 110G, the intensity of the emitted electromagnetic radiation from resonant structure 110R is increased and the intensity of the emitted electromagnetic radiation from resonant structure 110G is decreased. Likewise, the intensity of the emitted electromagnetic radiation from resonant structure 110R can be decreased and the intensity of the emitted electromagnetic radiation from resonant structure 110G can be increased by modifying the path of the beam 130 to become closer to the resonant structures 110G and farther away from the resonant structure 110R. In this way, a multi-resonant structure utilizing beam deflection can act as a wavelength or color channel mixer.

Figure 16:
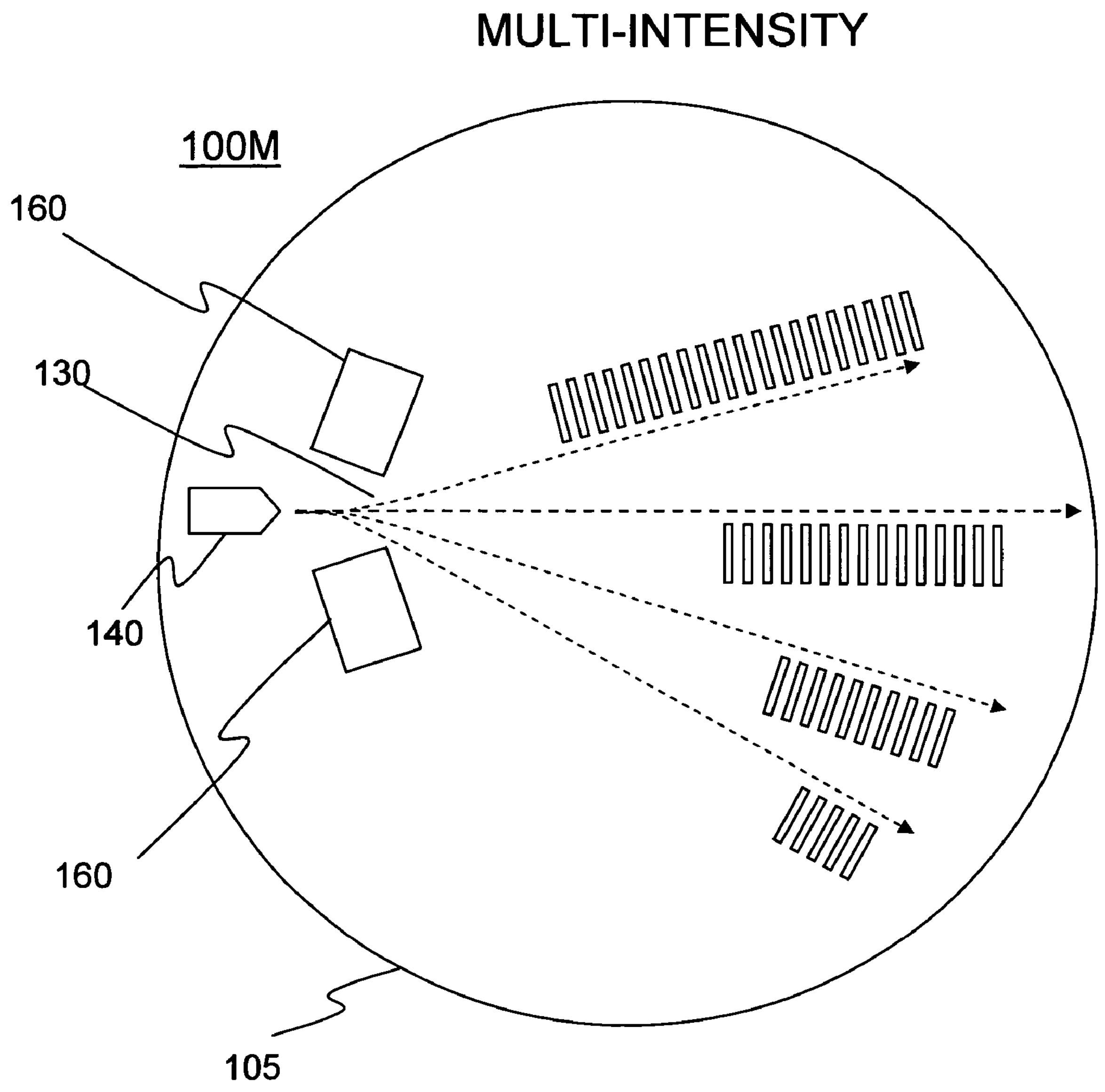
FIG. 16 is a top view of a multi-intensity element utilizing two deflectors according to another embodiment of the present invention.

As shown in FIG. 16, a multi-intensity pixel can be produced by providing plural resonant structures, each emitting the same dominant frequency, but with different intensities (e.g., based on different numbers of fingers per structure). As illustrated, the wavelength component is capable of providing five different intensities {off, 25%, 50%, 75% and 100%). Such a structure could be incorporated into a device having multiple multi-intensity elements 100 per color or wavelength.

The illustrated order of the resonant structures is not required and may be altered. For example, the most frequently used intensities may be placed such that they require lower amounts of deflection, thereby enabling the system to utilize, on average, less power for the deflection.

Figure 17A:
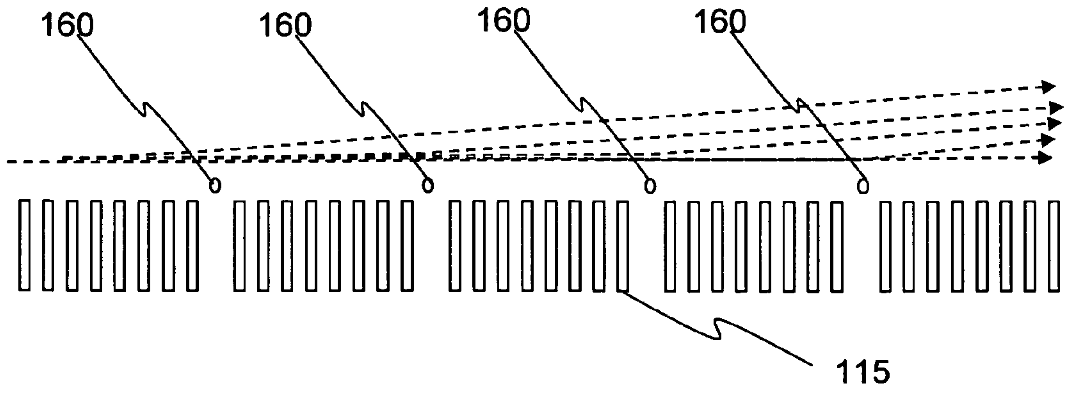
FIG. 17A is a top view of a multi-intensity element using plural inline deflectors.

As shown in FIG. 17A, the intensity can also be controlled using deflectors 160 that are inline with the fingers 115 and which repel the beam 130. By turning on the deflectors at the various locations, the beam 130 will reduce its interactions with later fingers 115 (i.e., fingers to the right in the figure). Thus, as illustrated, the beam can produce six different intensities {off, 20%, 40%, 60%, 80% and 100%} by turning the beam on and off and only using four deflectors, but in practice the number of deflectors can be significantly higher.

Figure 17B:
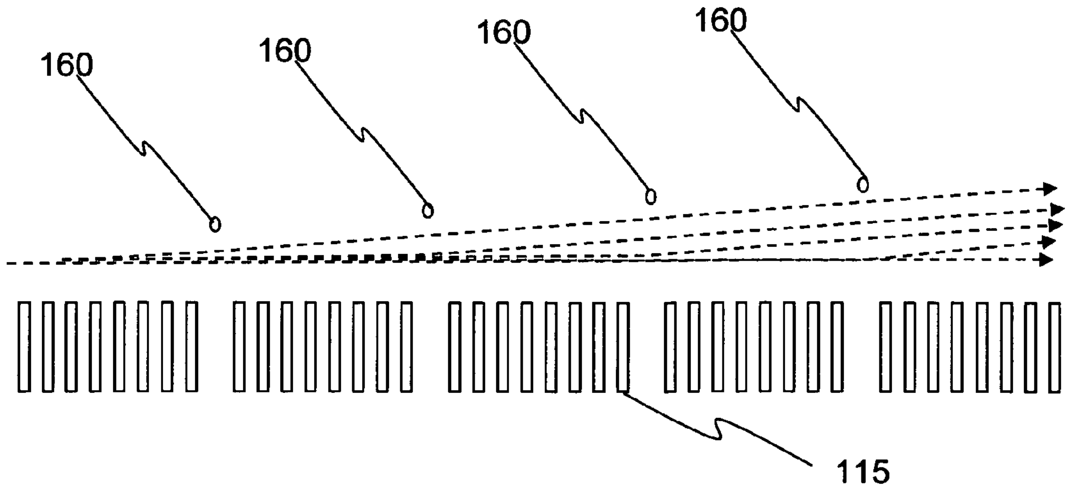
FIG. 17B is a top view of a multi-intensity element using plural attractive deflectors above the path of the beam.

Alternatively, as shown in FIG. 17B, a number of deflectors 160 can be used to attract the beam away from its undeflected path in order to change intensity as well.

Figure 17C:
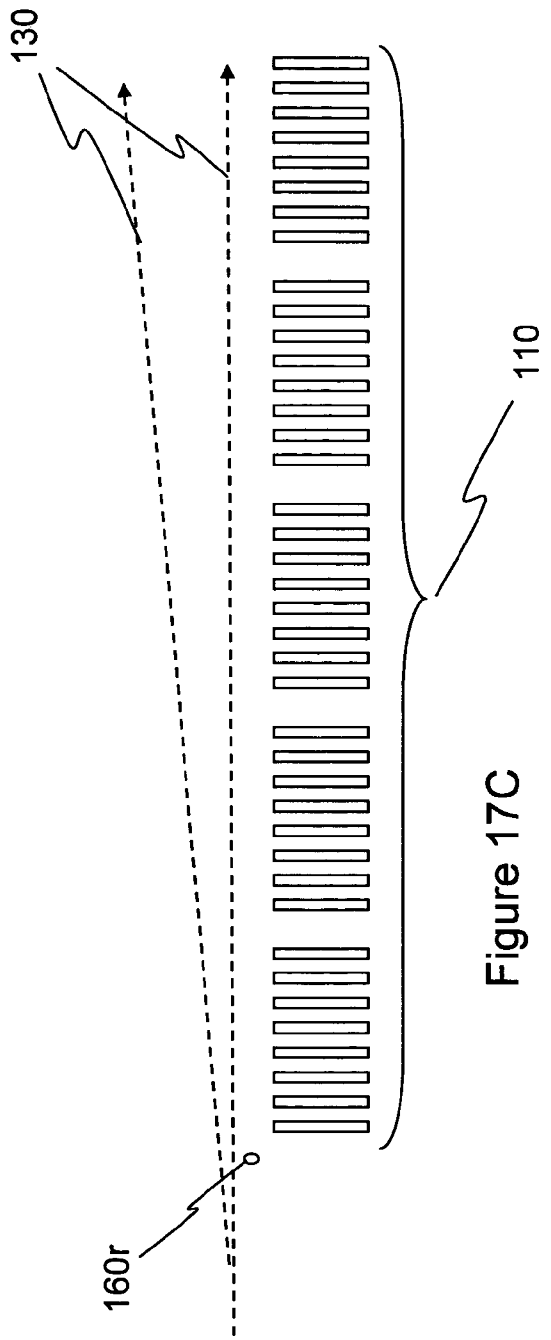
FIG. 17C is a view of a first deflectable beam for turning the resonant structures on and off without needing a separate data input on the source of charged particles and without having to turn off the source of charged particles.
Figure 17D:
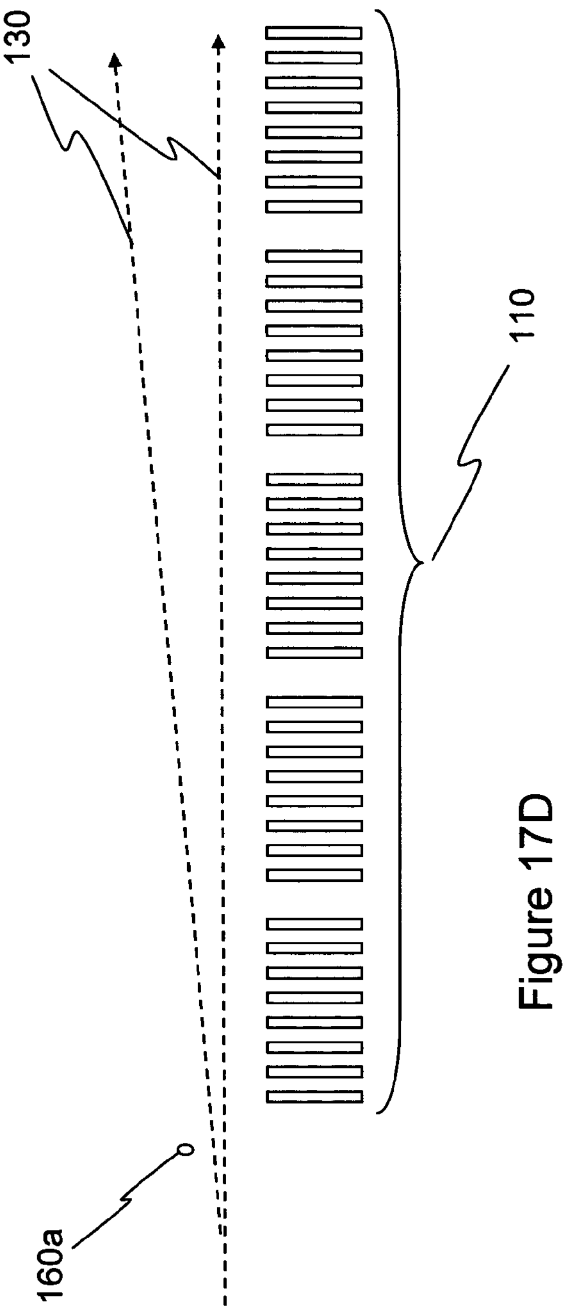
FIG. 17D is a view of a second deflectable beam for turning the resonant structures on and off without needing a separate data input on the source of charged particles and without having to turn off the source of charged particles.

In addition to the repulsive and attractive deflectors 160 of FIGS. 17A and 17B which are used to control intensity of multi-intensity resonators, at least one additional repulsive deflector 160*r* or at least one additional attractive deflector 160*a*, can be used to direct the beam 130 away from a resonant structure 110, as shown in FIGS. 17C and 17D, respectively. By directing the beam 130 before the resonant structure 110 is excited at all, the resonant structure 110 can be turned on and off, not just controlled in intensity, without having to turn off the source 140. Using this technique, the source 140 need not include a separate data input 145. Instead, the data input is simply integrated into the deflection control terminal 165 which controls the amount of deflection that the beam is to undergo, and the beam 130 is left on.

Furthermore, while FIGS. 17C and 17D illustrate that the beam 130 can be deflected by one deflector 160*a,r* before reaching the resonant structure 110, it should be understood that multiple deflectors may be used, either serially or in parallel. For example, deflector plates may be provided on both sides of the path of the charged particle beam 130 such that the beam 130 is cooperatively repelled and attracted simultaneously to turn off the resonant structure 110, or the deflector plates are turned off so that the beam 130 can, at least initially, be directed undeflected toward the resonant structure 110.

The configuration of FIGS. 17A-D is also intended to be general enough that the resonant structure 110 can be either a vertical structure such that the beam 130 passes over the resonant structure 110 or a horizontal structure such that the beam 130 passes next to the resonant structure 110. In the vertical configuration, the "off" state can be achieved by deflecting the beam 130 above the resonant structure 110 but at a height higher than can excite the resonant structure. In the horizontal configuration, the "off" state can be achieved by deflecting the beam 130 next to the resonant structure 110 but at a distance greater than can excite the resonant structure.

Alternatively, both the vertical and horizontal resonant structures can be turned "off" by deflecting the beam away from resonant structures in a direction other than the undeflected direction. For example, in the vertical configuration, the resonant structure can be turned off by deflecting the beam left or right so that it no longer passes over top of the resonant structure. Looking at the exemplary structure of FIG. 7, the off-state may be selected to be any one of: a deflection between 110B and 110G, a deflection between 110B and 110R, a deflection to the right of 110B, and a deflection to the left of 110R. Similarly, a horizontal resonant structure may be turned off by passing the beam next to the structure but higher than the height of the fingers such that the resonant structure is not excited.

In yet another embodiment, the deflectors may utilize a combination of horizontal and vertical deflections such that the intensity is controlled by deflecting the beam in a first direction but the on/off state is controlled by deflecting the beam in a second direction.

Figure 18A:
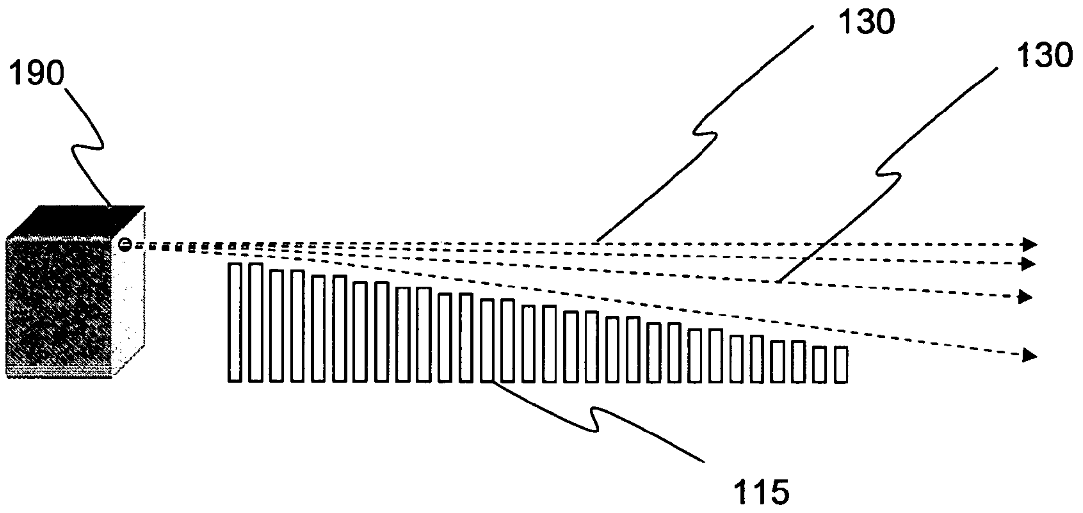
FIG. 18A is a top view of a multi-intensity element using finger of varying heights.

FIG. 18A illustrates yet another possible embodiment of a varying intensity resonant structure. (The change in heights of the fingers have been over exaggerated for illustrative purposes). As shown in FIG. 18A, a beam 130 is not deflected and interacts with a few fingers to produce a first low intensity output. However, as at least one deflector (not shown) internal to or above the source 190 increases the amount of deflection that the beam-undergoes, the beam interacts with an increasing number of fingers and results in a higher intensity output.

Figure 18B:
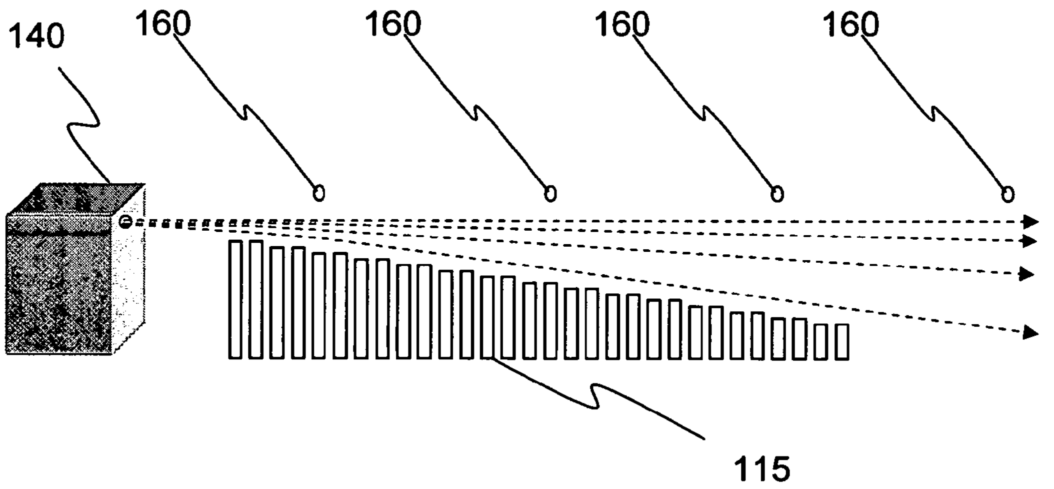
FIG. 18B is a top view of a multi-intensity element using finger of varying heights.

Alternatively, as shown in FIG. 18B, a number of deflectors can be placed along a path of the beam 130 to push the beam down towards as many additional segments as needed for the specified intensity.

While deflectors 160 have been illustrated in FIGS. 17A-18B as being above the resonant structures when the beam 130 passes over the structures, it should be understood that in embodiments where the beam 130 passes next to the structures, the deflectors can instead be next to the resonant structures.

Figure 19A:
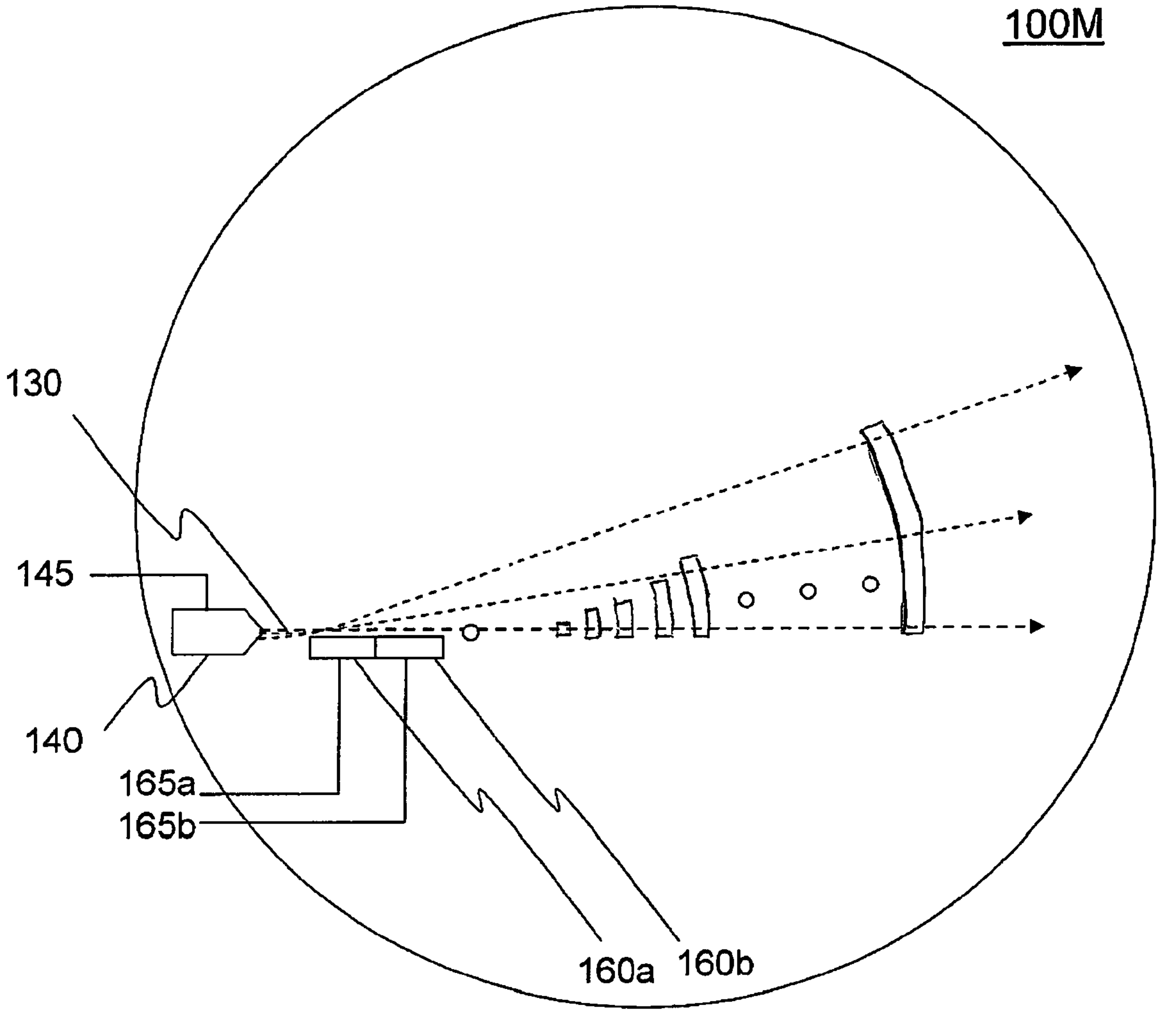
FIG. 19A is a top view of a fan-shaped resonant element that enables varying intensity based on the amount of deflection of the beam.
Figure 19B:
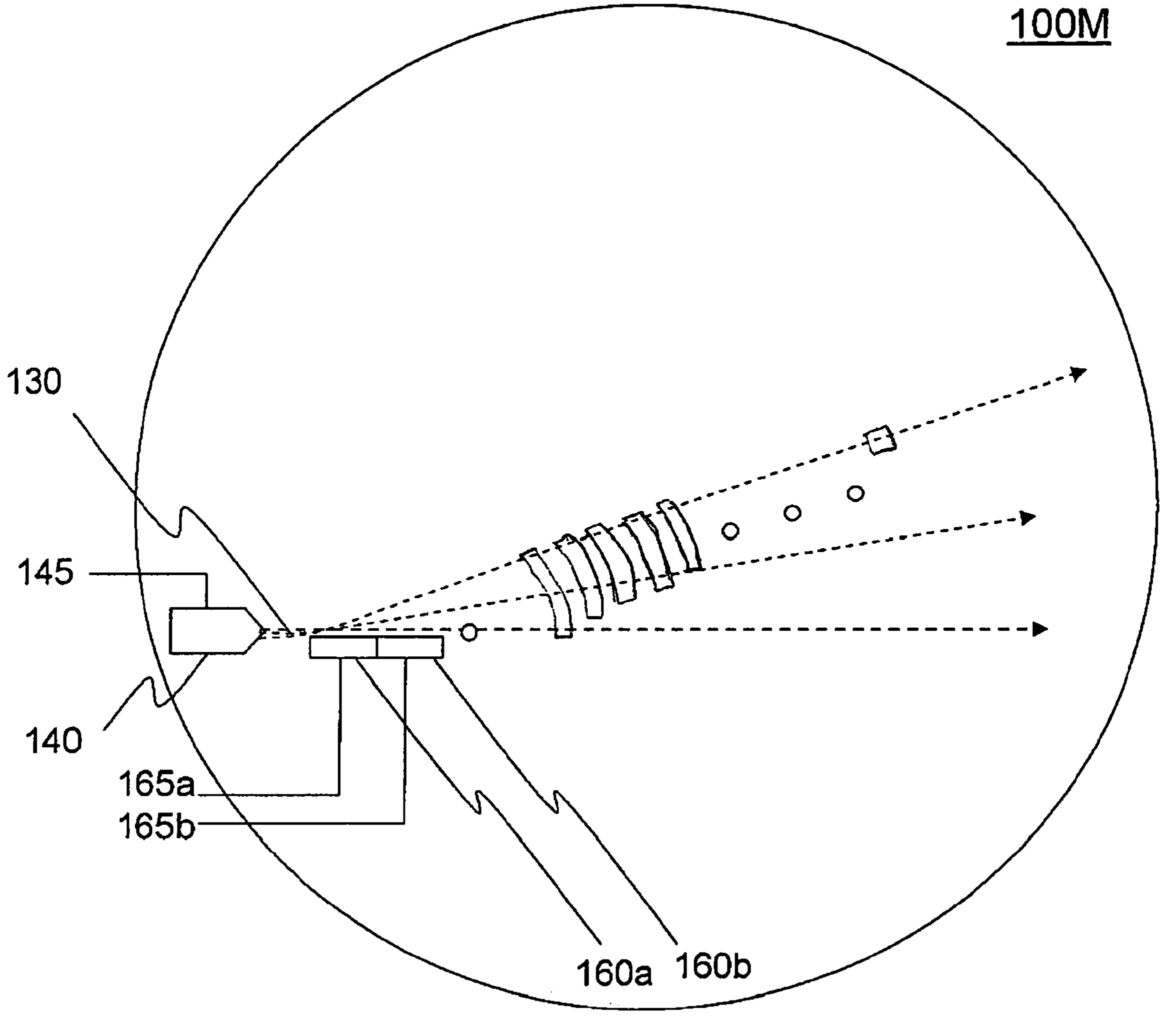
FIG. 19B is a top view of another fan-shaped resonant element that enables varying intensity based on the amount of deflection of the beam.

FIG. 19A illustrates an additional possible embodiment of a varying intensity resonant structure according to the present invention. According to the illustrated embodiment, segments shaped as arcs are provided with varying lengths but with a fixed spacing between arcs such that a desired frequency is emitted. (For illustrative purposes, the number of segments has been greatly reduced. In practice, the number of segments could be significantly greater, e.g., utilizing hundreds of segments.) By varying the lengths, the number of segments that are excited by the deflected beam changes with the angle of deflection. Thus, the intensity changes with the angle of deflection as well. For example, a deflection angle of zero excites 100% of the segments. However, at half the maximum angle 50% of the segments are excited. At the maximum angle, the minimum number of segments are excited. FIG. 19B provides an alternate structure to the structure of FIG. 19A but where a deflection angle of zero excites the minimum number of segments and at the maximum angle, the maximum number of segments are excited While the above has been discussed in terms of elements emitting red, green and blue light, the present invention is not so limited. The resonant structures may be utilized to produce a desired wavelength by selecting the appropriate parameters (e.g., beam velocity, finger length, finger period, finger height, duty cycle of finger period, etc.). Moreover, while the above was discussed with respect to three-wavelengths per element, any number (n) of wavelengths can be utilized per element.

As should be appreciated by those of ordinary skill in the art, the emissions produced by the resonant structures 110 can additionally be directed in a desired direction or otherwise altered using any one or a combination of: mirrors, lenses and filters.

The resonant structures (e.g., 110R, 110G and 110B) are processed onto a substrate 105 (FIG. 3) (such as a semiconductor substrate or a circuit board) and can provide a large number of rows in a real estate area commensurate in size with an electrical pad (e.g., a copper pad).

The resonant structures discussed above may be used for actual visible light production at variable frequencies. Such applications include any light producing application where incandescent, fluorescent, halogen, semiconductor, or other light-producing device is employed. By putting a number of resonant structures of varying geometries onto the same substrate 105, light of virtually any frequency can be realized by aiming an electron beam at selected ones of the rows.

Figure 20:
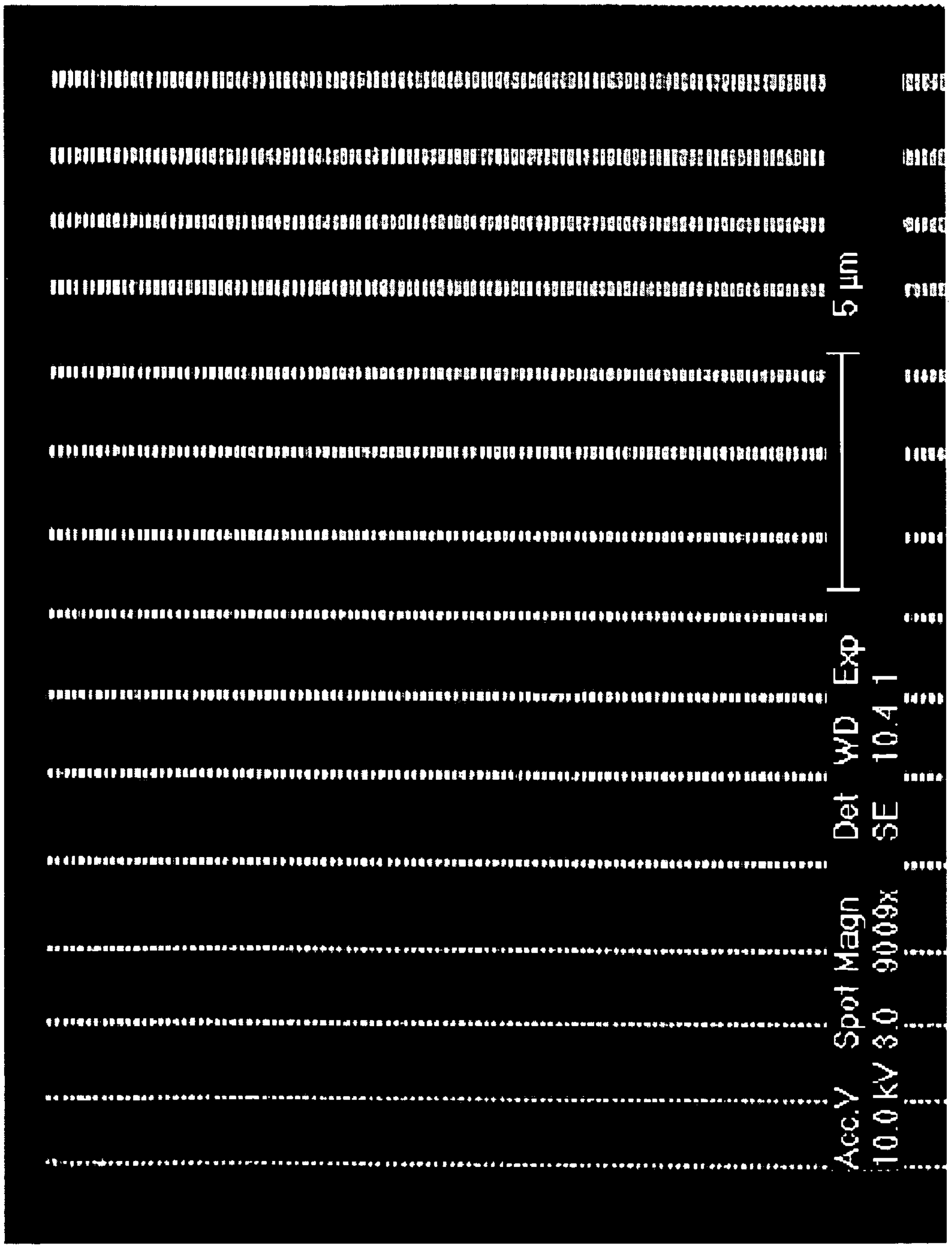
FIG. 20 is a microscopic photograph of a series of resonant segments.

FIG. 20 shows a series of resonant posts that have been fabricated to act as segments in a test structure. As can be seen, segments can be fabricated having various dimensions.

The above discussion has been provided assuming an idealized set of conditions—i.e., that each resonant structure emits electromagnetic radiation having a single frequency.

However, in practice the resonant structures each emit EMR at a dominant frequency and at least one "noise" or undesired frequency. By selecting dimensions of the segments (e.g., by selecting proper spacing between resonant structures and lengths of the structures) such that the intensities of the noise frequencies are kept sufficiently low, an element 100 can be created that is applicable to the desired application or field of use. However, in some applications, it is also possible to factor in the estimate intensity of the noise from the various resonant structures and correct for it when selecting the number of resonant structures of each wavelength to turn on and at what intensity. For example, if red, green and blue resonant structures 110R, 110G and 100B, respectively, were known to emit (1) 10% green and 10% blue, (2) 10% red and 10% blue and (3) 10% red and 10% green, respectively, then a grey output at a selected level ($level_s$) could be achieved by requesting each resonant structure output $level_s/(1+0.1+0.1)$ or $level_s/1.2$.

Figure 21:
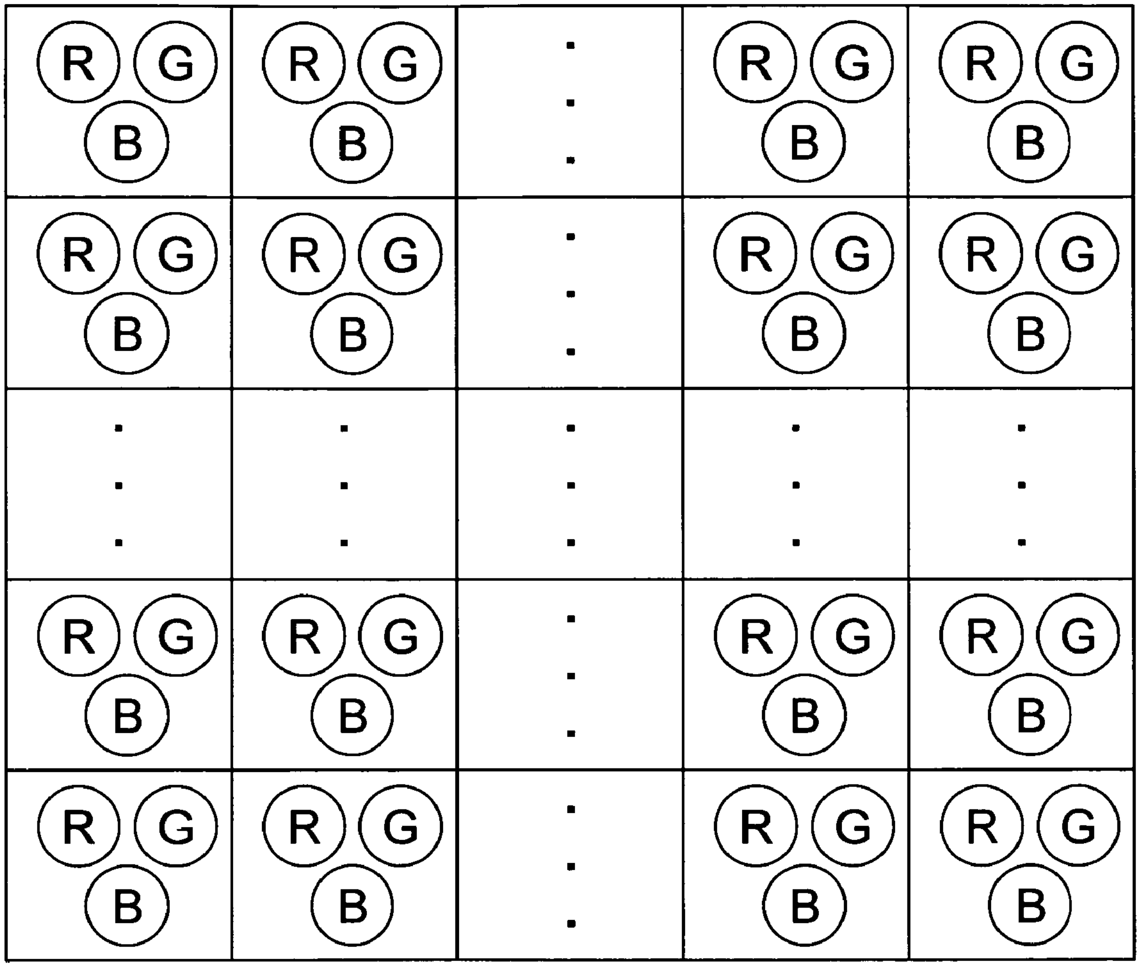
FIG. 21 is a generalized illustration of a display utilizing three wavelength elements per pixel.

Turning to FIG. 21, according to the present invention it is possible to build a black-and-white, a color or a grey-scale display from a series of resonant elements 100 that are excited by a beam 130 of charged particles, such as an electron beam. In the illustrated embodiment, each pixel is created by utilizing a group of elements emitting different frequencies (e.g., (1) red, green and blue in the visible portion of the electromagnetic radiation (EMR) spectrum or (2) other non-visible EMR such as infrared, ultraviolet and x-ray emissions). Known techniques enable groups of colors to be utilized as a black-and-white display by turning all three elements on equally to produce white, or off to produce black. Utilizing the same principle, other monochrome displays can be created by providing other elements or groups of elements that present a user with only a single wavelength and at a single intensity.

Alternatively, the structures of the present invention can be utilized to provide a grey-scale or varying intensity monochrome display by proportionally varying the intensity of groups of elements to provide a viewer with a wider range of possible images.

Figure 22:
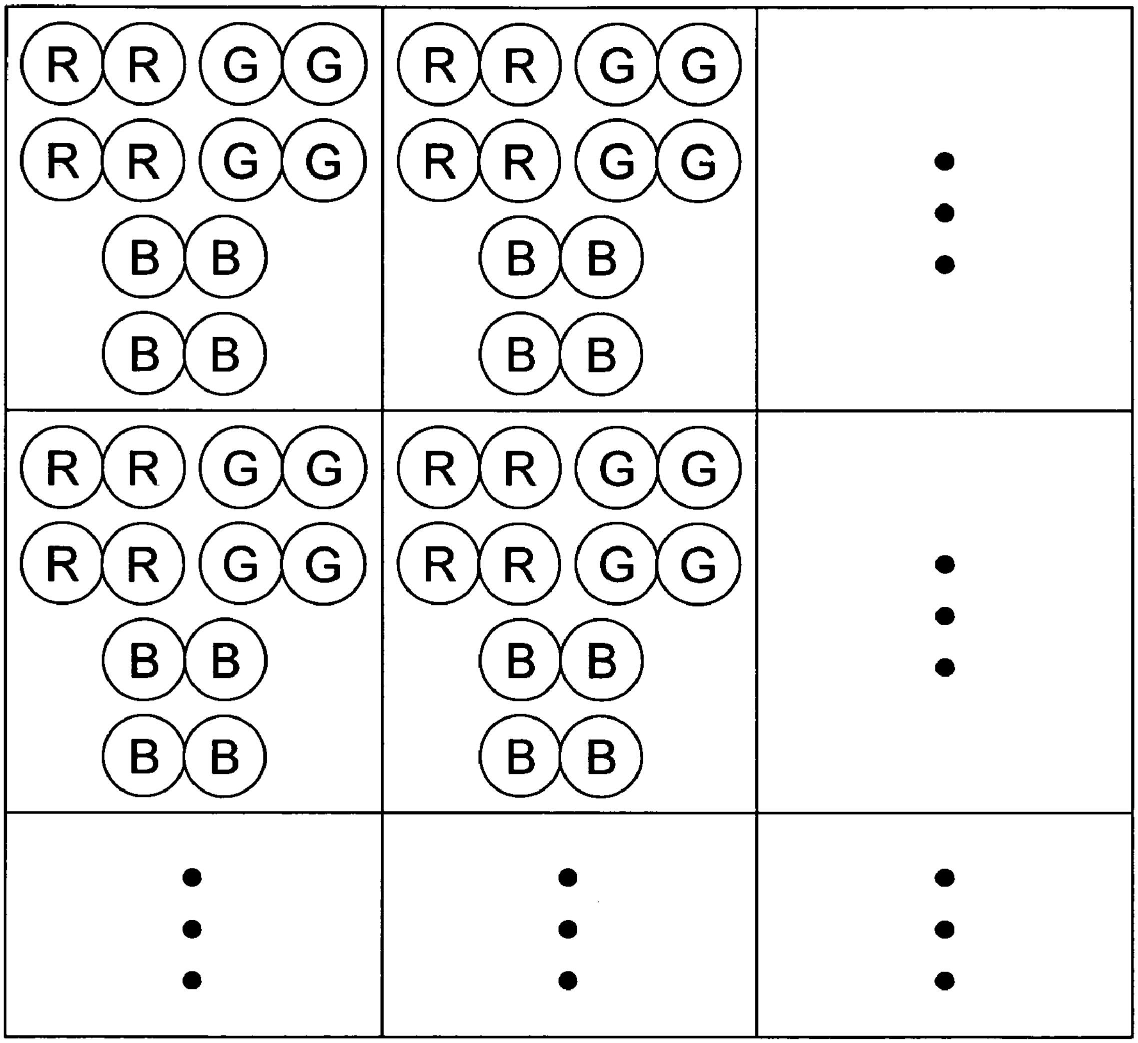
FIG. 22 is a generalized illustration of a display utilizing 12 wavelength elements per pixel with 4 elements per pixel illuminating the same wavelength.

As shown in FIG. 22, in yet another embodiment, a plurality of elements (illustrated as 4) of each wavelength (or a plurality of elements of plural wavelengths each) are utilized to enable further variations in the intensity of each wavelength. For example, to produce a grey of one intensity, only one element of each color (i.e., one red, one green and one blue element) is turned on. However, to produce a grey of a maximum intensity, all of the elements of each color (i.e., four red, four green and four blue elements) are turned on. Generally, the various shades of grey are produced by turning a proportional number of elements of each color on at the same intensity. For example, in an embodiment of FIG. 22, two red, green and blue elements each are turned on at full intensity and one red, green and blue element each are turned on at 50% intensity to produce a 2.5/4 or 62.5% intensity grey pixel.

When being used as a multi-frequency (or multi-wavelength) display, it is possible to control the intensities of pixels by providing plural resonant structures per wavelength per pixel and turning on the appropriate number of resonant structures to achieve the desired intensity. For example, for zero intensity (or "off") for a red component, none of the four resonant structures for red are turned on. For 25% red intensity, only one of the four resonant structures for red is turned on. For 50% red intensity, two of the four resonant structures for red are turned on, etc. However, due to the size of the structures described herein, hundreds or thousands of each wavelength component can be included in the same area as is currently occupied by a single pixel.

Displays of the structure of FIGS. 21 and 22 can be utilized in a large number of environments, such as televisions, computer monitors and generally electronic components and appliances. The use of these displays is also possible in heads-up displays. To facilitate fabrication of a heads-up display, a transparent conductor such as ITO may be used for some or all of the electrical connections, and a transparent substrate may be used.

As would be appreciated by those of ordinary skill in the art, if each pixel was represented by resonant structures of a multiplicity (m) of different wavelengths (e.g., m=3, 5, or 10), then providing multi-bit (e.g., 8-bit or 16-bit) intensity per wavelength component would provide an enormous number of possible wavelength combinations.

When producing a matrix such as is shown in FIGS. 21 and 22, the various pixels and their wavelength components can be laid out in a matrix of elements addressed by rows and columns corresponding to the pixel (or sub-pixel wavelength component) to be excited. In one such embodiment, the cathodes would be controlled with row lines and the anodes would be controlled with the column lines, or the other way around.

Additional details about the manufacture and use of such resonant structures are provided in the above-referenced co-pending applications, the contents of which are incorporated herein by reference.

The structures of the present invention may include a multi-pin structure. In one embodiment, two pins are used where the voltage between them is indicative of what frequency band, if any, should be emitted, but at a common intensity. In another embodiment, the frequency is selected on one pair of pins and the intensity is selected on another pair of pins (potentially sharing a common ground pin with the first pair). In a more digital configuration, commands may be sent to the device (1) to turn the transmission of EMR on and off, (2) to set the frequency to be emitted and/or (3) to set the intensity of the EMR to be emitted. A controller (not shown) receives the corresponding voltage(s) or commands on the pins and controls the director to select the appropriate resonant structure and optionally to produce the requested intensity.

While certain configurations of structures have been illustrated for the purposes of presenting the basic structures of the present invention, one of ordinary skill in the art will appreciate that other variations are possible which would still fall within the scope of the appended claims.

The invention claimed is:

1. In a display, the improvement comprising:

plural pixels each having at least one resonant structure per pixel, wherein the resonant structure is excited by a charged particle beam to produce electromagnetic radiation having a dominant frequency higher than that of a microwave, the resonant structure being formed of segments of resonating material having at least one spacing therebetween.

2. The display as claimed in claim 1, wherein the display is a computer monitor display.

3. The display as claimed in claim 1, wherein the display is a display of an electronics component.

4. The display as claimed in claim 1, the display is a television screen.

5. The display as claimed in claim 1, wherein each pixel utilizes three resonant structures per pixel.

6. The display as claimed in claim 1, wherein each pixel utilizes a first resonant structure producing red light, a second resonant structure producing green light and a third resonant structure producing blue light per pixel.

7. The display as claimed in claim 1, wherein the charged particle beam comprises a beam of electrons.

8. The display as claimed in claim 1, wherein the segments of resonating material comprise silver.

9. The display as claimed in claim 1, wherein the segments of resonating material comprise etched silver.

10. The display as claimed in claim 1, wherein the segments are post-shaped.

11. The display as claimed in claim 1, wherein the segments are connected by a backbone.

12. The display as claimed in claim 1, wherein the charged particle beam is passed over the plural resonant structures.

13. The display as claimed in claim 1, wherein the charged particle beam is passed next to the plural resonant structures.

14. The display as claimed in claim 1, wherein the plural resonant structures are formed from a single layer of resonating material.

15. The display as claimed in claim 14, wherein the single layer of resonating material comprises silver.

16. A display comprising:

plural pixels each having plural resonant structure per pixel, wherein the resonant structures are excited by at least one charged particle beam to produce electromagnetic radiation having a dominant frequency higher than that of a microwave, the resonant structures being formed of segments of resonating material having at least one spacing therebetween; and at least one deflector for selectively directing the at least one charged particle beam to activate a first one of the plural resonant structures to produce a first wavelength to be emitted from one of the plural pixels at a first time and to activate a second one of the plural resonant structures to produce a second wavelength to be emitted from one of the plural pixels at a second time.

* * * * *